United States Patent [19]

Fung et al.

[11] Patent Number: 5,032,577
[45] Date of Patent: Jul. 16, 1991

[54] PEPTIDYLAMINODIOLS

[75] Inventors: Anthony K. L. Fung, Waukegan; Dale J. Kempf, Lake Villa; Jay R. Luly; Saul H. Rosenberg; Jacob J. Plattner, all of Libertyville; all of Ill.

[73] Assignee: Abbott Laboratories, Abbott Park, Ill.

[21] Appl. No.: 132,356

[22] Filed: Dec. 18, 1987

Related U.S. Application Data

[63] Continuation-in-part of Ser. No. 943,567, Dec. 31, 1986, abandoned, which is a continuation-in-part of Ser. No. 895,009, Aug. 7, 1986, abandoned, which is a continuation-in-part of Ser. No. 818,734, Jan. 16, 1986, abandoned, which is a continuation-in-part of Ser. No. 693,951, Jan. 23, 1985, abandoned.

[51] Int. Cl.$^5$ .................. A61K 37/02; C07K 5/06; C07K 5/08
[52] U.S. Cl. .................. 514/18; 530/331; 530/332; 546/141; 546/146; 548/225; 548/344; 548/537; 564/153; 564/157
[58] Field of Search .................. 514/18, 19; 530/331, 530/332; 546/141, 146; 548/225, 344, 537; 564/153, 157

[56] References Cited

U.S. PATENT DOCUMENTS

| 4,548,926 | 10/1985 | Matsueda et al. | |
| 4,609,643 | 9/1986 | Szelke et al. | |
| 4,616,088 | 10/1986 | Ryono et al. | |
| 4,645,759 | 2/1987 | Luly et al. | |
| 4,652,551 | 3/1987 | Luly et al. | |
| 4,657,931 | 4/1987 | Baran et al. | 514/616 |
| 4,680,284 | 7/1987 | Luly et al. | |
| 4,698,329 | 10/1987 | Matsueda et al. | |
| 4,845,079 | 7/1989 | Luly et al. | 514/18 |
| 4,877,785 | 10/1989 | Hanson et al. | 514/224.2 |
| 4,900,746 | 2/1990 | Hanson et al. | 514/400 |
| 4,902,706 | 2/1990 | Hanson et al. | 514/400 |

FOREIGN PATENT DOCUMENTS 0202577 11/1986 European Pat. Off. .
0229667 7/1987 European Pat. Off. .

OTHER PUBLICATIONS

Burger, Medicinal Chemistry, 1960, pp. 565-571, 578-581, 600-601.

Denkewalter et al., Progress in Drug Research, vol. 10, 1966, pp. 510-512.
Plattner et al, J. Med. Chem. 31(12) 2277-2288, 1988.
Thaisrivongs et al., J. Med. Chem. 1987, 30(6) 976-982.
Hanson et al., Biochem. Biophys. Res. Comm. 1985, 132(1) 155-161.
Matsueda et al., Chem. Lett., 1044, (1985).
T. Kokubu et al., Hypertension 8(6) (Suppl. II), II-I, (1986).
S. Thaisrivongs, et al., J. Med. Chem. 28 1555, (1985).
G. Hanson et al., Biochem. Biophys. Res. Commun. 132, 155, (1985).
Weber et al., Renin Inhibition in Hypertension, vol. 81, No. 6, Jun. 1990, pp. 1768-1774.

Primary Examiner—Lester L. Lee
Assistant Examiner—Stephen B. Maebius
Attorney, Agent, or Firm—Steven R. Crowley

[57] ABSTRACT

A renin inhibiting compound of the formula:

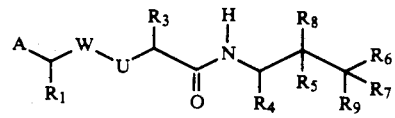

wherein A is a substituent; W is C=O or CHOH; U is $CH_2$ or $NR_2$, provided that when W is CHOH then U is $CH_2$; $R_1$ is loweralkyl, cycloalkylmethyl, benzyl, 4-methoxybenzyl, halobenzyl, (1-naphthyl)methyl, (2-naphthyl)methyl, (4-imidazoyl)methyl, (alpha,alpha)-dimethylbenzyl, 1-benzyloxyethyl, phenethyl, phenoxy, thiophenoxy or anilino; $R_2$ is hydrogen or loweralkyl; $R_3$ is loweralkenyl, [(alkoxy)alkoxy]alkyl, (thioalkoxy)alkyl, loweralkenyl, benzyl or heterocyclic ring substituted methyl; $R_4$ is loweralkyl, cycloalkylmethyl or benzyl; $R_5$ is vinyl, formyl, hydroxymethyl or hydrogen; $R_7$ is hydrogen or loweralkyl; $R_8$ and $R_9$ are independently selected from OH and $NH_2$; and $R_6$ is hydrogen, loweralkyl, vinyl or arylalkyl; provided that when $R_5$ and $R_7$ are both hydrogen and $R_8$ and $R_9$ are OH, the carbon bearing $R_5$ is of the "R" configuration and the carbon bearing $R_6$ is of the "S" configuration, or pharmaceutically acceptable salts or esters thereof. Also disclosed are renin inhibiting compositions, a method of treating hypertension, methods of making the renin inhibiting compounds and intermediates useful in making the renin inhibiting compounds.

10 Claims, No Drawings

PEPTIDYLAMINODIOLS

TECHNICAL FIELD

This is a continuation-in-part of U.S patent application Ser. No 943,567, filed Dec. 31, 1986, which is a continuation-in-part of U.S. patent application Ser. No 895,009, filed Aug. 7, 1986, which is a continuation-in-part of U.S. patent application Ser. No 818,734, filed Jan. 16, 1986, which is a continuation-in-part of U.S patent application, Ser. No. 693,951, filed Jan. 23, 1985.

The present invention relates to novel organic compounds and compositions which inhibit renin, processes for making such compound, synthetic intermediates employed in these processes and a method of treating hypertension with such compounds.

BACKGROUND ART

Renin is a proteolytic enzyme synthesized and stored principally in a specific part of the kidney called the juxtaglomerular apparatus Any of three different physiologic circumstances may cause the release of renin into the circulation (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated. leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (Nature, Vol. 303, p. 81, 1983). In addition, Szelke and co-workers have described polypeptide analogs containing a non-peptide link (Nature, Vol. 299, p. 555, 1982) which also cause potent renin inhibition and show a high specificity for this enzyme.

DISCLOSURE OF THE INVENTION

In accordance with the present invention, there are renin inhibiting compounds of the formula:

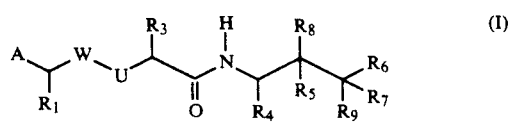

wherein A is hydrogen; loweralkyl; arylalkyl; OR$_{10}$ or SR$_{10}$ wherein R$_{10}$ is hydrogen, loweralkyl or aminoalkyl; NR$_{11}$R$_{12}$ wherein R$_{11}$ and R$_{12}$ are independently selected from hydrogen, loweralkyl, aminoalkyl, cyanoalkyl, hydroxyalkyl, carboxyalkyl, alkoxycarbonylalkyl, (amino)carboxyalkyl, [(N-protected)amino]carboxyalkyl, (alkylamino)carboxyalkyl, [(N-protected)alkylamino]carboxyalkyl, (dialkylamino)carboxyalkyl, (amino)alkoxycarbonylalkyl, [(N-protected)amino]alkoxycarbonylalkyl, (alkylamino)alkoxycarbonylalkyl, [(N-protected)alkylamino]-alkoxycarbonylalkyl and (dialkylamino)alkoxycarbonylalkyl;

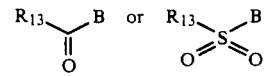

wherein B is NH, alkylamino, S, O, CH$_2$ or CHOH and R$_{13}$ is loweralkyl, cycloalkyl, aryl, arylalkyl, alkoxy, alkenyloxy, hydroxyalkyl, dihydroxyalkoxy, arylalkoxy, arylalkoxyalkyl, amino, alkylamino, dialkylamino, (hydroxyalkyl)(alkyl)amino, (dihydroxyalkyl)(alkyl)amino aminoalkyl, N-protected-aminoalkyl, alkylaminoalkyl, (N-protected)(alkyl)aminoalkyl, dialkylaminoalkyl, carboxyalkoxyalkyl, (alkoxycarbonyl)alkoxyalkyl, carboxyalkyl, carboxyalkylamino, alkoxycarbonylalkyl, alkoxycarbonylalkylamino, (amino)carboxyalkyl, (amino)carboxyalkylamino, [(N-protected)amino]carboxyalkyl, [(N-protected)amino]carboxyalkyamino, (alkylamino)carboxyalkyl, (alkylamino)carboxyalkylamino, [(N-protected)alkylamino]carboxyalkyl, [(N-protected)alkylamino]carboxyalkyamino, (dialkylamino)carboxyalkyl, (dialkylamino)carboxyalkylamino, (amino)alkoxycarbonylalkyl, (amino)alkoxycarbonylalkylamino, [(N-protected)amino]alkoxycarbonylalkyl, [(N-protected)amino]alkoxycarbonylalkylamino, (alkylamino)alkoxycarbonylalkyl, (alkylamino)alkoxycarbonylalkylamino, [(N-protected)alkylamino]alkoxycarbonylalkyl, [(N-protected)alkylamino]alkoxycarbonylalkylamino, (dialkylamino)alkoxycarbonylalkyl, (dialkylamino)alkoxycarbonylalkylamino, aminocycloalkyl, aminoalkylamino, dialkylaminoalkyl(alkyl)amino, arylalkylamino, arylalkyl(alkyl)amino, alkoxyalkyl(alkyl)amino, (polyalkyoxy)alkyl(alkyl)amino, di-(alkoxyalkyl)amino, di-(hydroxyalkyl)amino, di-[(polyalkoxy)alkyl]amino, polyalkoxy, (polyalkoxy)alkyl, (heterocyclic)alkyl or a substituted or unsubstituted heterocyclic wherein saturated heterocyclics may be unsubstituted, monosubstituted or disubstituted with hydroxy, oxo, amino, alkylamino, dialkylamino, alkoxy, polyalkoxy or loweralkyl; unsaturated heterocyclics may be unsubstituted or monosubstituted with hydroxy, amino, alkylamino, dialkylamino, alkoxy, polyalkoxy or loweralkyl;

W is C=O or CHOH;

U is $CH_2$ or $NR_2$, provided that when W is CHOH then U is $CH_2$;

$R_1$ is loweralkyl, cycloalkylmethyl, benzyl, 4-methoxybenzyl, halobenzyl, (1-naphthyl)methyl, (2-naphthyl)methyl, (4-imidazoyl)methyl, (alpha,alpha)-dimethylbenzyl, 1-benzyloxyethyl, phenethyl, phenoxy, thiophenoxy or anilino; provided if $R_1$ is phenoxy, thiophenoxy or anilino, B is $CH_2$ or CHOH or A is hydrogen; $R_2$ is hydrogen or loweralkyl; $R_3$ is loweralkyl, loweralkenyl, [(alkoxy)alkoxy]loweralkyl, (thioalkoxy)alkyl, benzyl or heterocyclic ring substituted methyl; $R_4$ is loweralkyl, cycloalkylmethyl or benzyl; $R_5$ is vinyl, formyl, hydroxymethyl or hydrogen; $R_7$ is hydrogen or loweralkyl; $R_8$ and $R_9$ are independently selected from OH and $NH_2$; and $R_6$ is hydrogen, loweralkyl, vinyl or arylalkyl; provided that when $R_5$ and $R_7$ are both hydrogen and $R_8$ and $R_9$ are OH, the carbon bearing $R_5$ is of a "R" configuration and the carbon bearing $R_6$ is of a "S" configuration; or pharmaceutically acceptable salts or erters thereof.

The chiral centers of the compounds of the invention may have either the "R" or "S" configuration but preferably have an "S" configuration except where noted. The terms "S" and "R" configuration are as defined by the IUPAC 1974 Recommendations for Section E, Fundamental Stereochemistry, Pure Appl. Chem. (1976) 45, 13-30.

The term "N-protecting group" or "N-protected" as used herein refers to those groups intended to protect nitrogen atoms against undesirable reactions during synthetic procedures or to prevent the attack of exopeptidases on the final compounds or to increase the solubility of the final compounds and includes but is not limited to acyl, acetyl, pivaloyl, t-butylacetyl, t-butyloxycarbonyl(Boc), benzyloxycarbonyl (Cbz)or benzoyl groups or an L- or D- aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "loweralkenyl" as used herein refers to a loweralkyl radical which contains at least one carbon-carbon double bond.

The term "arylalkyl" as used herein refers to an unsubstituted or substituted aromatic ring appended to an alkyl radical including but not limited to benzyl, 1- and 2-naphthylmethyl, halobenzyl and alkoxybenzyl.

The term "aminoalkyl" as used herein refers to $-NH_2$ appended to a loweralkyl radical.

The term "cyanoalkyl" as used herein refers to -CN appended to a loweralkyl radical.

The term "hydroxyalkyl" as used herein refers to -OH appended to a loweralkyl radical.

The term "alkylamino" as used herein refers to a loweralkyl radical appended to an NH radical.

The term "cycloalkyl" as used herein refers to an aliphatic ring having 4 to 7 carbon atoms.

The term "cycloalkylmethyl" as used herein refers to an cycloalkyl group appended to a methyl radical, including but not limited to cyclohexylmethyl.

The term "aryl" as used herein refers to a substituted or unsubstituted aromatic ring including but not limited to phenyl, naphthyl, halophenyl and alkoxyphenyl.

The terms "alkoxy" and "thioalkoxy" as used herein refer to $R_{14}O-$ and $R_{14}S-$, respectively, wherein $R_{14}$ is a loweralkyl group.

The term "alkenyloxy" as used herein refers to $R_{15}O-$ wherein $R_{15}$ is an unsaturated alkyl group.

The term "hydroxyalkoxy" as used herein refers to -OH appended to an alkoxy radical.

The term "dihydroxyalkoxy" as used herein refers to an alkoxy radical which is disubstituted with -OH radicals.

The term "arylalkoxy" as used herein refers to an aryl appended to an alkoxy radical.

The term "arylalkoxyalkyl" as used herein refers to an arylalkoxy appended to a loweralkyl radical.

The term "(thioalkoxy)alkyl" as used herein refers to thioalkoxy appended to a loweralkyl radical.

The term "dialkylamino" as used herein refers to $-NR_{16}R_{17}$ wherein $R_{16}$ and $R_{17}$ are independently selected from loweralkyl groups.

The term "[(alkoxy)alkoxy]alkyl" refers to an alkoxy group appended to an alkoxy group which is appended to a loweralkyl radical.

The term "(hydroxyalkyl)(alkyl)amino" as used herein refers to $-NR_{18}R_{19}$ wherein $R_{18}$ is hydroxyalkyl and $R_{19}$ is loweralkyl.

The term "N-protected aminoalkyl" as used herein refers to $NHR_{20}$ appended to a loweralkyl group, wherein $R_{20}$ is an N-protecting group.

The term "alkylaminoalkyl" as used herein refers to $NHR_{21}$ appended to a loweralkyl radical, wherein $R_{21}$ is a loweralkyl group.

The term "(N-protected)(alkyl)aminoalkyl" as used herein refers to $NR_{20}R_{21}$, which is appended to a loweralkyl radical, wherein $R_{20}$ and $R_{21}$ are as defined above.

The term "dialkylaminoalkyl" as used herein refers to $NR_{22}R_{23}$ is appended to a loweralkyl radical wherein $R_{22}$ and $R_{23}$ are independently selected from loweralkyl.

The term "carboxyalkyl" as used herein refers to a carboxylic acid group (-COOH) appended to a loweralkyl radical.

The term "alkoxycarbonylalkyl" as used herein refers to $R_{24}COR_{25}-$ wherein $R_{24}$ is an alkoxy group and $R_{25}$ is a loweralkyl radical.

The term "carboxyalkoxyalkyl" as used herein refers to a carboxylic acid group (-COOH) appended to an alkoxy group which is appended to a loweralkyl radical.

The term "alkoxycarbonylalkoxyalkyl" as used herein refers to an alkoxycarbonyl group ($R_{26}CO-$ wherein $R_{26}$ is an alkoxy group) appended to an alkoxy group which is appended to a loweralkyl radical.

The term "(amino)carboxyalkyl" as used herein refers to a loweralkyl radical to which is appended a carboxylic acid group (-COOH) and an amino group ($-NH_2$).

The term "[(N-protected)amino]carboxyalkyl" as used herein refers to a loweralkyl radical to which is appended a carboxylic acid group (-COOH) and $-NHR_{27}$ wherein $R_{27}$ is an N-protecting group.

The term "(alkylamino)carboxyalkyl" as used herein refers to a loweralkyl radical to which is appended a carboxylic acid group (—COOH) and an alkylamino group.

The term "[(N-protected)alkylamino]carboxyalkyl" as used herein refers to a loweralkyl radical to which is appended a carboxylic acid group (—COOH) and an —$NR_{27}R_{28}$ wherein $R_{27}$ is as defined above and $R_{28}$ is a loweralkyl group.

The term "(dialkylamino)carboxyalkyl" as used herein refers to a loweralkyl radical to which is appended a carboxylic acid group (—COOH) and —$NR_{28}R_{28}$ wherein $R_{28}$ is as defined above.

The term "(amino)alkoxycarbonylalkyl" as used herein refers to a loweralkyl radical to which is appended an alkoxycarbonyl group as defined above and an amino group (—$NH_2$)

The term "[(N-protected)amino]alkoxycarbonylalkyl" as used herein refers to a loweralkyl radical to which is appended an alkoxycarbonyl group as defined above and —$NHR_{27}$ wherein $R_{27}$ is as defined above.

The term "(alkylamino)alkoxycarbonylalkyl" as used herein refers to a loweralkyl radical to which is appended an alkoxycarbonyl group as defined above and an alkylamino group as defined above.

The term "[(N-protected)alkylamino]alkoxycarbonylalkyl" as used herein refers to a loweralkyl radical to which is appended an alkoxycarbonyl group as defined above and —$NR_{27}R_{28}$ wherein $R_{27}$ and $R_{28}$ are as defined above.

The term "(dialkylamino)alkoxycarbonyalkyl" as used herein refers to a loweralkyl radical to which is appended an alkoxycarbonyl group as defined above and —$NR_{28}R_{28}$ wherein $R_{28}$ is as defined above.

The term "carboxyalkylamino" as used herein refers to —$NHR_{29}$ wherein $R_{29}$ is a carboxyalkyl group.

The term "alkoxycarbonylalkylamino" as used herein refers to —$NHR_{30}$ wherein $R_{30}$ is an alkoxycarbonylalkyl group.

The term "(amino)carboxyalkylamino" as used herein refers to —$NHR_{31}$ wherein $R_{31}$ is an (amino)carboxyalkyl group.

The term "[(N-protected)amino]carboxyalkylamino" as used herein refers to —$NHR_{32}$ wherein $R_{32}$ is an [(N-protected)amino]carboxyalkyl group.

The term "(alkylamino)carboxyalkylamino" as used herein refers to —$NHR_{33}$ wherein $R_{33}$ is an (alkylamino)carboxyalkyl group.

The term "[(N-protected)alkylamino]carboxyalkylamino" as used herein refers to —$NHR_{34}$ wherein $R_{34}$ is an [(N-protected)alkylamino]carboxyalkyl group.

The term "(dialkylamino)carboxyalkylamino" as used herein refers to —$NHR_{35}$ wherein $R_{35}$ is a (dialkylamino)carboxyalkyl group.

The term "(amino)alkoxycarbonylalkylamino" as used herein refers to —$NHR_{36}$ wherein $R_{36}$ is an (amino)alkoxycarbonylalkyl group.

The term "[(N-protected)amino]alkoxycarbonylalkylamino" as used herein refers to —$NHR_{37}$ wherein $R_{37}$ is an [(N-protected)amino]alkoxycarbonylalkyl group.

The term "(alkylamino)alkoxycarbonylalkylamino" as used herein refers to —$NHR_{38}$ wherein $R_{38}$ is an (alkylamino)alkoxycarbonylalkyl group.

The term "[(N-protected)alkylamino]alkoxycarbonylalkylamino" as used herein refers to —$NHR_{39}$ wherein $R_{39}$ is an [(N-protected)alkylamino]alkoxycarbonylalkyl group.

The term "(dialkylamino)alkoxycarbonylalkylamino" as used herein refers to —$NHR_{40}$ wherein $R_{40}$ is a (dialkylamino)alkoxycarbonylalkyl group.

The term "aminocycloalkyl" as used herein refers to an $NH_2$ appended to a cycloalkyl radical.

The term "[(alkoxy)alkoxy]alkyl" as used herein refers to an alkoxy group appended to an alkoxy group which is appended to a loweralkyl radical.

The term "polyalkoxyalkyl" as used herein refers to a polyalkoxy residue appended to a loweralkyl radical.

The term "polyalkoxy" as used herein refers to —$OR_{41}$ wherein $R_{41}$ is a straight or branched chain containing 1-5, $C_n$-O-$C_{n'}$ linkages wherein n and n' are independently selected from 1 to 3.

The term "arylalkylamino" as used herein refers to —$NHR_{42}$ wherein $R_{42}$ is an arylalkyl residue.

The term "arylalkyl(alkyl)amino" as used herein refers to —$NR_{43}R_{44}$ wherein $R_{43}$ is an arylalkyl residue and $R_{44}$ is a loweralkyl residue.

The term "dialkylaminoalkyl(alkyl)amino" as used herein refers to —$NR_{45}R_{46}$ wherein $R_{45}$ is a dialkylamino residue appended to a loweralkyl residue and $R_{46}$ is a loweralkyl residue.

The term "aminoalkylamino" as used herein refers to —$NHR_{47}$ wherein $R_{47}$ is an aminoalkyl residue.

The term "(dihydroxyalkyl)(alkyl)amino" as used herein refers to a loweralkyl group which is disubstituted with -OH radicals, appended to an amino group, which amino group also has appended another loweralkyl group.

The term "di-(hydroxyalkyl)amino" as used herein refers to —$NR_{48}R_{49}$ wherein $R_{48}$ and $R_{49}$ are hydroxyalkyl residues.

The term "alkoxyalkyl(alkyl)amino" as used herein refers to —$NR_{50}R_{51}$ wherein $R_{50}$ is an alkoxyalkyl group and $R_{51}$ is a loweralkyl group.

The term "di-(alkoxyalkyl)amino" as used herein refers to —$NR_{52}R_{53}$ wherein $R_{52}$ and $R_{53}$ are alkoxyalkyl groups.

The term "di-(polyalkoxyalkyl)amino" as used herein refers to —$NR_{54}R_{55}$ wherein $R_{54}$ and $R_{55}$ are polyalkoxy residues appended to loweralkyl residues.

The term [(polyalkoxy)alkyl](alkyl)amino" as used herein refers to —$NR_{56}R_{57}$ wherein $R_{56}$ is a polyalkoxy residue appended to a loweralkyl residue and $R_{57}$ is a loweralkyl residue.

The term "(heterocyclic)alkyl" as used herein refers to a heterocyclic group appended to a loweralkyl radical, including but not limited to imidazolylalkyl and thiazolylalkyl.

The term "O-protecting group" as used herein refers to a substituent which protects hydroxyl groups and includes but is not limited to substituted methyl ethers, for example, methoxymethyl, benzyloxymethyl, 2-methoxyethoxymethyl, 2-(trimethylsilyl)ethoxymethyl and tehahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "heterocyclic ring" or "heterocyclic" as used herein refers to any 5- or 6-membered ring containing from one to three heteroatoms selected from the group consisting of nitrogen, oxygen, and sulfur; wherein the 5-membered ring has 0-2 double bonds and the 6-membered ring has 0-3 double bonds; wherein the nitrogen and sulfur heteroatoms may optionally be oxidized; wherein the nitrogen heteroatom may optionally be quaternized; and including any bicyclic group in which any of the above heterocyclic rings is fused to a benzene ring. Heterocyclics in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Saturated heterocyclics may be unsubstituted, monosubstituted or disubstituted with hydroxy, oxo, amino, alkylamino, dialkylamino, alkoxy, polyalkoxy or loweralkyl. Unsaturated heterocyclics may be unsubstituted or monosubstituted with hydroxy, amino, alkylamino, dialkylamino, alkoxy, polyalkoxy or loweralkyl.

The most preferred heterocyclics are as follows:

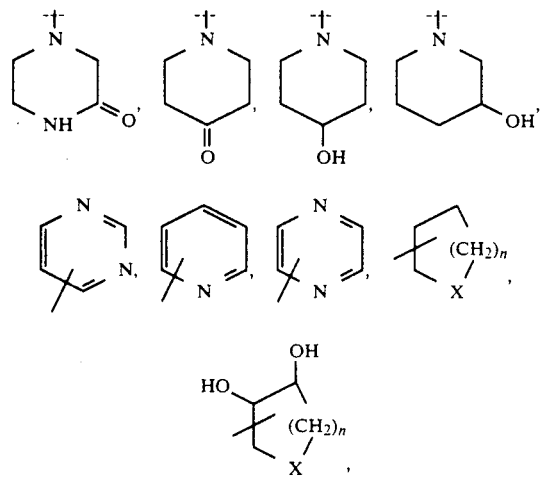

wherein n is 1 or 2 and X is N, NH, O, S, provided that X is the point of connection only when X is N,

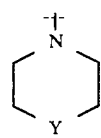

wherein Y is NH, N-loweralkyl, O, S, or SO₂, or

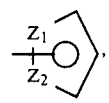 (i)

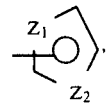 (ii)

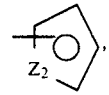 (iii)

wherein the symbols (i), (ii) and (III) represent 5-membered heterocycles containing one or more heteroatoms and containing 2 double bonds; wherein $Z_1$ is N, O, or S and not the point of connection and $Z_2$ is N when it is the point of connection and NH, O or S when it is not the point of connection.

The terms "Ala", "His", "Leu", "Phe", "Tyr", "Cys", "Gly", "LYs", "Sar" and "Pro" as used herein refer to alanine. histidine. leucine. phenylalanine, tyrosine, cysteine, glycine, lysine, sarcosine and proline, respectively.

Most of the compounds of the invention may be made as shown in Scheme I The amino diol intermediate 5 represents a transition-state mimic for the Leu-Val scissile bond of the renin substrate, angiotensinogen Incorporation of this amine into the angiotensinogen sequence in place of Leu-Val-Ile-Protein provides potent inhibitors of human renin. For example. acylation of amine 5 with an acyl-Phe-His-OH residue or other appropriately modified amino acid derivatives produces small peptide analogues which are potent renin inhibitors.

SCHEME I

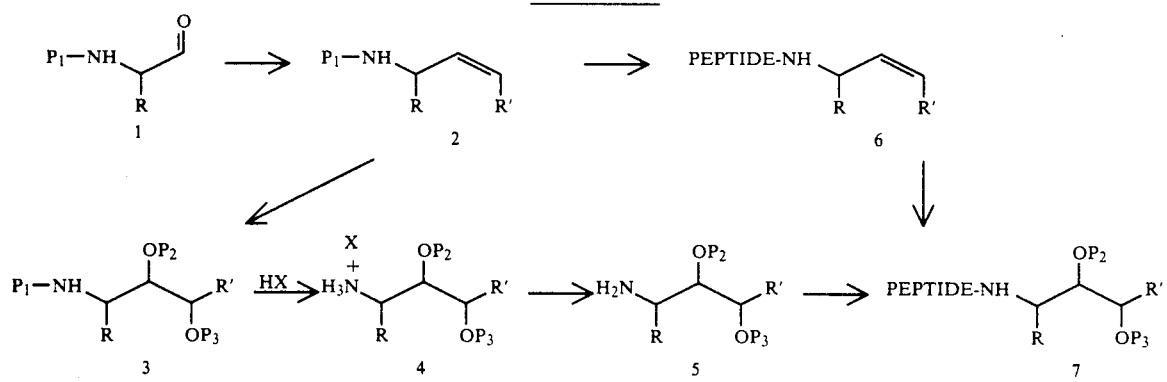

$P_1$ is an N-protecting group; $P_2$ and $P_3$ are independently selected from hydrogen or an O-protecting group.
R is loweralkyl, cycloadlkylmethyl or benzyl.

R' is hydrogen, loweralkyl, vinyl or arylalkyl.
HX is an acid.

More particularly, the process shown in Scheme I discloses an N-protected-aminoaldehyde 1 ($P_1$ is an N-protecting group) which is treated with an ylide to give the corresponding allylic amine 2. Oxidation gives diol 3 ($P_2$ and $P_3$ are both hydrogen), N-deprotection gives 4; and free-basing gives amine 5. Either intermediate 4 or 5 can be converted to 7 by standard peptide coupling methods. The same seguence (3-7) can be carried out with hydroxy protecting groups present (where $P_2$ and/or $P_3$ are O-protecting groups), the final step then being O-deprotection. Alternatively, allylic amine 2 may be N-deprotected, peptide coupled using standard methods to give 6, and then oxidized to give the desired peptide diols 7.

The protected aminodiol fragment may be alternatively prepared as shown in Scheme II. Aldehyde 9 (prepared, for example, by oxidation of alcohol 8) is converted to its cyanohydrin 10. Addition of an organometallic reagent (such as a Grignard reagent) and acidic workup provides ketone 12. Reduction of ketone 12 then provides the desired protected aminodiol 13.

($MgSO_4$), filtered, and evaporated. The residue was purified by chromatography (40 m $SiO_2$; ether:hexane, 15:85) to give the desired compound in 60% yield. Mass spectrum: $(M+H)^+ = 254$.

EXAMPLE 2

Boc-Phe-Ala Amide of (2S)-Amino-1-cyclohexylbut-3-ene

The resultant compound of Example 1 (310 mg, 1.22 mmol) was dissolved in 1 M anhydrous HCl in anhydrous methanol (35 mL). After 22 hours, the solvent was evaporated to give 230 mg (99%) of the corresponding amine hydrochloride which was used without further purification.

To a stirred $-13°$ C. solution of Boc-phe-Ala (408 mg, 1.21 mmol) in dry THF (8 mL) containing N-methylmorpholine (122 mg, 1.21 mmol) was added isobutyl chloroformate (165 mg, 1.21 mmol) dropwise. After 3 minutes, a $-13°$ C. solution of the above amine hydrochleride (230 mg, 1.21 mmol) in 1:1, THF:dimethyl formamide (DMF) (4 mL) containing

SCHEME II

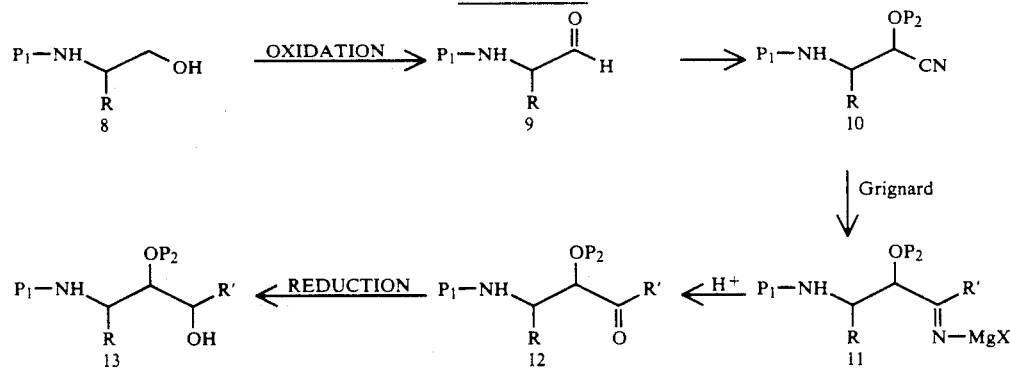

$P_1$, $P_2$, R and R' are as defined for Scheme I, except that R' cannot be hydrogen.

The following Examples will serve to further illustrate preparation of the novel compounds of the invention.

EXAMPLE 1

2(S)-t-Butyloxycarbonylamino-1-cyclohexylbut-3-ene

A 0° C. solution of potassium hexamethyldisilazide (22.9 mmol in 115 mL of 5:1, tetrahydrofuran (THF): dimethyl sulfoxide (DMSO) was added dropwise to triphenylmethylphosphonium iodide (24.81 mmol). After stirring at 0° C. for 1 hour, the solution was cooled to $-78°$ C. and a solution of Boc-cyclohexylalaninal [4.90 g. 19.08 mmol, prepared by Swern oxidation (Mancuso, A. J.; Huang,, S. -L.; and Swern, D., *J. Org. Chem.* 1978, 43, 2480) of Boc-cyclohexylalaninol] in dry THF (95 mL) was added. After stirring at $-78°$ C. for 1 hour, the mixture was allowed to warm to room temperature. The reaction mixture was quenched with aqueous ammonium chloride and extracted with ether (2×300 mL). The combined organic phase was washed with 10% HCl (200 mL), saturated $NaHSO_3$ (2×200 mL), $H_2O$ (2×200 mL), saturated $NaHCO_3$ (2×200 mL), and brine (200 mL), dried N-methylmorpholine (122 mg) was added dropwise. The mixture was warmed to room temperature for 2 hours. Evaporation provided a residue which was partitioned between ethyl acetate (30 mL) and 0.1 M $H_3PO_4$ (10 mL). The organic phase was washed with brine (10 mL), saturated $NaHCO_3$ (10 mL), and brine (10 mL). Drying, filtering, evaporating, and chromatographing (55 g $SiO_2$; 95:5, $CH_2Cl_2$:$CH_3OH$) gave the desired compound (462 mg, 81%).

EXAMPLE 3

Boc-Phe-Ala Amide of 3(S)-Amino-4-cyclohexyl-1,2(R,S)-dihydroxybutane

To a stirred solution of the resultant compound of Example 2 (100 mg, 0.212 mmol) in THF (5 mL) were added $OsO_4$ solution (0.065 mL of a 2.5 W/V % solution in t-butanol) and N-methylmorpholine N-oxide (57 mg, 0.424 mmol) seguentially. After 4.5 hours, brine (10 mL) was added, and the mixture was extracted with ether (4×8 mL). The combined organic phase was washed with 10% $Na_2SO_3$ (3×6 mL), 0.1 M $H_3PO_4$ (5 mL), and brine (5 mL). Drying, filtering, and evaporat-

EXAMPLE 4

3(S)-t-Butyloxycarbonylamino-4-cyclohexyl-1,2(R,S)-dihydroxybutane

To a stirred solution of 2(S)-t-butyloxycarbonylamino-1-cyclohexylbut-3-ene (1.00 g, 3.95 mmol) in THF (20 mL) were added $OsO_4$ solution (1.2 mL of a 2.5 W/V % solution in t-butanol) and N-methylmorpholine N-oxide (1.07 g, 7.90 mmol). After 24 hours, the mixture was partitioned between ether (50 mL) and brine (25 mL). The layers were separated, and the organic phase was extracted with ether (3×25 mL). The combined organic phase was washed with 10% $Na_2SO_3$ (4×10 mL), 1.0 M $H_3PO_4$ (2×8 mL) and brine (15 mL). Drying and evaporating provided the desired product as an oil (1.14 g, 100%). H NMR shows a 1:1 mixture of diastereomers (NH 4.43 and 4.56 ppm).

EXAMPLE 5

Boc-Phe-His Amides of 3(S)-Amino-4-cyclohexyl-2(R,S)-hydroxy-1-t-butyldimethylsilyloxybutane The resultant compound of Example 4 (1.10 g, 3.82 mmol) was treated with anhydrous 1M $HCl/CH_3OH$ (80 mL) for 16 hours at which time evaporation and drying provided the corresponding amine hydrochloride (0.85 g, 100%).

To a suspension of the above hydrochloride salt (344 mg, 1.54 mmol) and imidazole (105 mg) in dichloromethane (15 mL) were added triethylamine (156 mg) and t-butyldimethylsilyl chloride (232 mg). The solvent was evaporated after 31 hours, and the residue was then re-dissolved in anhydrous dimethylformamide (DMF, 15 mL). Boc-Phe3His (619 mg) and 1-hydroxybenzotriazole (HOBT, 312 mg) were then added. After cooling the stirred solution to $-23°$ C., 1,3-dicyclohexylcarbodiimide (DCC, 318 mg) was added. The mixture was warmed to room temperature 3 hours later. After 13 hours the solvent was evaporated in vacuo, and the residue was dissolved in ethyl acetate (40 mL), filtered, washed with saturated $NaHCO_3$ (2×10 mL) and brine (10 mL), and dried ($Na_2SO_4$). Filtration and evaporation provided a residue which was chromatographed on silica gel eluting with dichloromethane/methanol mixtures to give 441 mg (42%) of the desired product. Mass spectrum: $(M+H)^+ = 686$.

Analysis calculated for $C_{36}H_{59}N_5O_6SI$: C, 63.0; H, 8.7; N, 10.2. Found: C, 62.8; H, 9.0; N, 9.9.

EXAMPLE 6

Boc-Phe-His Amides of 3(S)-Amino-4-cyclohexyl-1,2(R)-dihydroxybutane

To a stirred solution of the resultant product of Example 5 (200 mg, 0.291 mmol) in anhydrous THF (5 mL) at 0° C. was added tetrabutylammonium fluoride (0.58 mL of a 1 M solution in THF). The solution was warmed to room temperature for 4 hours and then evaporated. The residue was dissolved in chloroform and washed with water (3×) and brine (1×). Drying and evaporating provided a gum which was treated with hot ethyl acetate (8 mL). Cooling and filtration provided 25 mg of the desired material. Mass spectrum: $(M+H)^+ = 572$.

Anal. Calcd for $C_{30}H_{45}N_5O_6 \cdot \frac{1}{2} H_2O$: C, 62.1; H, 8.0; N, 12.1. Found: C, 62 4; H, 8.2; N, 12.0.

EXAMPLE 7

(4S)-2,8-Dimethyl-4-[(toluenesulfonyl)amino]-5-nonanone

To a stirred $-78°$ C. solution of toluenesulfonyl (Ts)-Leu (15 g, 53 mmol) in dry THF (240 mL) was added butyl lithium (57.8 mL of a 0.91 M solution in hexane) followed 15 minutes later by isopentyl magnesium bromide (185 mL of a 0.8 M solution in THF). The mixture was heated at reflux for 3 days, then cooled and poured into 0° C. 1 M HCl (500 mL). The layers were separated and the aqueous phase was extracted with ether (3×50 mL). The combined organic layers were washed with saturated $NaHCO_3$ (2×150 mL) and brine (150 mL). Drying and evaporating provided a residue which was chromatographed on silica gel to give 7.43 g (41%) of the desired product. Mass spectrum: $(M+H)^+ = 340$.

Analysis calculated for $C_{18}H_{29}NO_3S$: C, 63.7; H, 8.6; N, 4.1. Found: C, 64.0; H, 8.6; N, 4.1.

EXAMPLE 8

(4S)-2,8-Dimethyl-5-hydroxy-4-[(toluenesulfonyl)amino]-5-vinylnonane

To a stirred 0° C. solution of the resultant compound of Example 7 (79 mg, 0.23 mmol) in dry THF (8 mL) was added vinyl magnesium bromide (1.5 mL of a 1.0 M solution in THF) dropwise The mixture was warmed (room temperature, 10 hours), quenched (8 mL $H_2O + 2$ mL brine), acidified with 0.1 M H (pH=7), and extracted with ether (3×4 mL). The combined ether phase was washed (4 mL brine) dried ($Na_2SO_4$), filtered. and evaporated to give 81 mg (95%) of the desired product as a 4:1 mixture of diastereomers.

EXAMPLE 9

Boc-Phe-Ala Amide of (4S)-Amino-2,8-dimethyl-5-hydroxy-5-vinylnonane

To a solution of the resultant compound of Example 8 (400 mg, 1.09 mmol) in liquid ammonia (80 mL) was added sodium (150 mg, 6.5 mmol). After 6 hours the ammonia was allowed to slowly evaporate under a stream of nitrogen. Benzene (50 mL) and 1:1, ethanol:-water (20 mL) were added with stirring. The layers were separated, and the aqueous phase was extracted with ether. The combined organic phase was dried ($Na_2SO_4$), filtered, and evaporated to give 85 mg (37%) of the desired product.

Following the procedure of Example 2, but replacing the amine hydrochloride and N-methylmorpholine with the above resultant product, gave the desired major diastereomer in 35% yield after chromatography. FAB mass spectrum: $(M+K)^+ = 570$.

Anal. calcd. for $C_{30}H_{49}N_3O_5$: % C, 67.8; H, 9.3; N, 7.9. Found: C, 67.7; H, 9.6; N, 7.3.

EXAMPLE 10

Boc-Phe-Ala Amide of (3S)-Amino-2-hydroxy-2-isopentyl-5-methylhexanal

Following the procedure of Example 3 with the resultant compound of Example 9 except replacing N-methylmorpholine N-oxide with aqueous $NaIO_4$ gave the desired compound.

EXAMPLE 11

Boc-Phe-Ala Amide of 3-Amino-1,2-dihydroxy-2-isopentyl-5-methylhexane

Treatment of the resultant compound of Example 10 with one equivalent of NaBH$_4$ in methanol provided the desired compound after aqueous work-up.

EXAMPLE 12

Boc-Phe-Ala Amide of 3-Amino-1,2-dihydroxy-2-isopentyl-5-methylhexane

Scale up of the procedure of Example 8 led to the isolation of the minor diastereomer pure after chromatography. Treatment as in Examples 9, 10, and 11 provided the desired isomer of the resultant product of Example 11.

EXAMPLE 13

2(S)-t-Butyloxycarbonylamino-1-cyclohexyl-6-methyl-hept-3-ene

To a stirred −78° C. solution of Boc-cyclohexylalanine methyl ester (40 g, 140 mmol) in anhydrous toluene (250 mL) was added diisobutylaluminum hydride (130 M %, 1.5 M solution in toluene, 121.4 mL) at a rate to keep the internal temperature below −60° C. After stirring for an additional 20 minutes at −78° C., the aldehyde solution is used immediately as described below.

To a potassium hydride (35% dispersion in oil, 32.09 g) suspension in a 0° C. mixture of anhydrous THF/DMSO (1000 mL/200 mL) under dry N$_2$ was added 1,1,1,3,3,3-hexamethyldisilazane (209 M %, 49.07 g) dropwise. After stirring at 0° C. for 1 hour, the resulting solution was added via cannula to a 0° C. flask containing isopentyltriphenylphosphonium bromide (209 M %, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 mL) followed by aqueous Rochelle salts (100 mL saturated solution and 500 mL H$_2$O). The mixture was then extracted with ethyl acetate (2×). The combined extracts were washed with water and brine. Drying (MgSO$_4$) and evaporating provided crude alkene which was chromatographed on silica gel (ether/hexane) to give 16.5 g (38%) of the desired compound as an 85:15 mixture of cis:trans isomers. Mp=53°–55° C. Mass spectrum: M+ =309.

Analysis calculated for C$_{19}$H$_{35}$NO$_2$: C, 73.7; H, 11.4; N, 4.5. Found: C, 73.8; H, 11.4; N, 4.5.

EXAMPLE 14

2(S)-t-Butyloxycarbonylamino-1-cyclohexyl-3,4-dihydroxy-6-methylheptane: The 3(R)4(S), 3(S)4(S), 3(R)4(R), and 3(S)4(R) Diastereomers To a solution of the resultant compound of Example 13 (8.50, 27.5 mmol) in dry THF (150 mL) were added OsO$_4$ (2.8 mL of a 2.5% solution in t-butanol and N-methylmorpholine N-oxide (9.28 g, 68.7 mmol). After 4 days the mixture was partitioned between ether (200 mL) and brine (100 mL). The aqueous layer was back-extracted with ether (2×100 mL), and the combined organic phase was washed with 10% Na$_2$SO$_3$, 0.1 jM H$_3$PO$_4$, and brine. Drying (MgSO$_4$) and evaporating provided a residue (10.81 g) which was chromatographed on silica gel to elute a 60% yield of the 4 diols in the following order.

3(R),4(S) Mass spectrum: (M+H)$^+$ =344. Anal. calcd. for C$_{19}$H$_{37}$NO$_4$: C, 66.4; H, 10.9; N, 4.1. Found: C, 66.4; H, 10.8; N, 3.9.

3(S),4(S) Mass spectrum: (M+H)$^+$ =344. Anal. calcd. for C$_{19}$H$_{37}$NO$_4$: C, 66.4; H, 10.9; N, 5.1. Found: C, 66.4; H, 11.1; N, 4.0.

3(R),4(R) Mass spectrum: (M+H)$^+$ =344.

3(S),4(R) Mass spectrum: (M+H)$^+$ =344. Anal. calcd. for C$_{19}$H$_{37}$NO$_4$: C, 66.4; H, 10.9; N, 4.1. Found: C, 66.0; H, 10.7; N, 4.0.

EXAMPLE 15

Boc-Phe-His Amide of 2(S)-Amino-1-cyclohexyl-3(R),4(S)-dihydroxy-6-methylheptane The 3(R),4(S) diastereomer of Example 14 was deprotected with HCl/methanol, and the resulting product was coupled to Boc-Phe-His using 1-hydroxybenzotriazole and 1,3-dicyclohexylcarbodiimide according to the procedure of Example 5. The desired product was obtained in 40–60% yield. Mass spectrum: (M+H)$^+$ =628.

Anal. calcd. for C$_{34}$H$_{53}$N$_5$O$_6$ H$_2$O: C, 63.2; H, 8.6; N, 10.8. Found: C, 63.2; H, 8.4; N, 10.5.

EXAMPLE 16

Boc-Phe-His Amide of 2(S)-Amino-1-cyclohexyl-3(S),4(S)-dihydroxy-6-methylheptane Following the procedure of Example 15, but replacing the 3(R),4(S) diastereomer with the 3(S),4(S) diastereomer gave the desired compound. Mass spectrum: (M+H)$^+$ =628.

Anal. calcd. for C$_{34}$H$_{53}$N$_5$O$_6$ ½ H$_2$O: C, 64.1; H, 8 6; N, 11.0. Found: C, 64.0; H. 8.6; N, 10.6.

EXAMPLE 17

Boc-Phe-His Amide of 2(S)-Amino-1-cyclohexyl-3(R),4(R)-dihydroxy-6-methylheptane Following the procedure of Example 15, but replacing the 3(R),4(S) diastereomer with the 3(R),4(R) diastereomer gave the desired compound. Mass spectrum: (M+H)$^+$ =628.

Anal. calcd. for C$_{34}$H$_{53}$N$_5$O$_6$ H$_2$O: C, 63.2; H, 8.6; N, 10.8. Found: C, 63.1; H, 8.5; N, 10.7.

EXAMPLE 18

Boc-Phe-His Amide of 2(S)-Amino-1-cyclohexyl-3(S),4(R)-dihydroxy-6-methylheptane Following the procedure of Example 15, but replacing the 3(R),4(S) diastereomer with the 3(S),4(R) diastereomer gave the desired compound. Mass spectrum: (M+H)$^+$ =628.

Anal. calcd. for C$_{34}$H$_{53}$N$_5$O$_6$ ¾ H$_2$O: C, 63.7; H, 8.6; N, 10.9. Found: C, 63.8; H, 8.8; N, 10.7.

EXAMPLE 19

A.
4(S)-t-Butyloxycarbonylamino-5-cyclohexyl-3(R,S)-hydroxy-1-pentene

To a stirred −78° C. solution of Boc-cyclohexylalanine methyl ester (10.2 g, 35.8 mmol) in dry toluene (60 mL) was added diisobutylaluminum hydride (34 mL of a 1.5 M solution in toluene). After 30 minutes, vinyl magnesium bromide (108 mL of 1 M solution in THF) was added. After stirring for 15 hours at 0° C., the mixture was carefully quenched with methanol, treated with Rochelle salts (22 mL of saturated aqueous solution in 140 mL $H_2O$), and filtered. After extracting the solids 5 times with ethyl acetate, the extracts and filtrate were combined and the organic phase was washed with brine, dried, filtered, and evaporated to an oil (10.2 g). Chromatography on silica gel eluting with hexane/ethyl acetate mixtures provided 6.1 g (60%) of the desired product.

Anal. calcd. for $C_{16}H_{29}NO_3 \cdot \frac{1}{4} H_2O$: C, 6.8; H, 10.3; N, 4.9. Found: C, 66.9; H, 10.2; N, 4.7.

B.
4(S)-Cyclohexylmethyl-5(R,S)-vinyl-2-oxazolidinone

The resultant product of Example 19A (2.80 g, 9.88 mmol) in dry dimethylformamide (DMF) (50 mL) was added to a stirred suspension of NaH (593 mg of a 60% dispersion in oil, 14.8 mmol, hexane washed) in dry DMF (50 mL). After 3 hours, the mixture was quenched (750 mL water + 100 mL brine) and extracted with ether (5 × 100 mL). The combined organic phase was washed with brine (3 × 50 mL), dried (MgSO$_4$), filtered, and evaporated to an oil 2.23 g. The NMR spectrum of the crude product revealed an 82:18 mixture of 5 S:5 R diastereomers. Silica gel chromatography gave 80% recovery of pure diastereomers. 5 S:

Anal. calcd. for $C_{12}H_{19}NO_2$: C, 68.9; H, 9.1; N, 6.7. Found: 68.4; H, 9.2; N, 6.5. Mass spectrum: $(M+1)^+ = 210$. 5 R: Mass spectrum: $(M+1)^+ = 210$.

C.
5(R)-Carboxy-4(S)-cyclohexylmethyl-2-oxazolidinone

To a solution of the compound from Example 19B (1 g, 4.78 mmol) dissolved in 16 mL of benzene and 3 mL of acetic acid was added a solution of 3.01 g of potassium permanganate in 16 mL of water. The resultant two-phase mixture was vigorously stirred and treated by portionwise addition with 153 mg of tetrabutylammonium bromide. After stirring for 2 hours at room temperature, the mixture was quenched with aqueous sodium bisulfite, acidified to pH = 3, and extracted with ethyl acetate. Drying and evaporating gave the desired product as an oil in 59% yield.

D.
4(S)-Cyclohexylmethyl-5(R)-[3-(3-hydroxypentyl)]-2-oxazolidinone

To a solution of the compound from Example 19C dissolved in tetrahydrofuran and cooled to −78° C. was added 3.5 equivalents of ethyl magnesium bromide. After stirring at −78° C. for 1.5 hours and at room temperature for 1 hour, the reaction mixture was quenched with water and extracted with ether. The dried ethereal extract was evaporated to afford a 73% yield of product.

E.
2(S)-Amino-1-cyclohexyl-3(R)-3,4-dihydroxy-4-ethylhexane

A solution of the compound from Example 19D (1.69 mmol) and barium hydroxide octahydrate (3.38 mmol) in dioxane (60 mL) and water (40 mL) was heated at reflux under $N_2$ for 21 hours. The solid barium carbonate was filtered and the filtrate was partially evaporated. The residue was diluted with water and the resulting solution was extracted with ether. The organic extract was washed with brine solution, dried over MgSO$_4$, and evaporated to give the desired product in 76% yield.

F. Boc-Phe-His Amide of 2(S)-Amino-1-cyclohexyl-3(R)-3,4-dihydroxy-4-ethylhexane The resultant product of Example 19E was coupled to Boc-Phe-His using 1-hydroxybenzotriazole and 1,3-dicyclohexylcarbodiimide according to the procedure of Example 5 to give the desired product in 55% yield

EXAMPLE 20

Boc-His Amide of 2(S)-Amino-1-cyclohexyl-3(R),4(S)-dihydroxy-6-methylheptane The procedure of Example 15 was followed except Boc-Phe-His was replaced with Boc-His. Mass spectrum: $(M)^+ = 480$.

Anal. calcd. for $C_{25}H_{44}N_4O_5 \cdot \frac{3}{4} H_2O$: C, 60.8; H, 9.1; N, 11.3. Found: C, 60.9; H, 9.2; N, 11.0.

EXAMPLE 21

TBA-CHA-His Amide of 2(S)-Amino-1-cyclohexyl-3(R),4(S)-dihydroxy-6-methylheptane The resultant compound of Example 20 was deprotected with HCl/methanol, and the resulting product was coupled to t-butylacetyl-cyclohexylalanine (TBA-CHA) using the DCC/HOBT method of Example 5. HRMS calcd. for $C_{35}H_{61}N_5O_5$, (M + H) 632.4751. Found: 632.4759.

EXAMPLE 22

Ethoxycarbonyl-(OCH$_3$)Tyr-His Amide of 2(S)-Amino-1-cyclohexyl-3(R),4(S)-dihydroxy-6-methylheptane Using the procedure of Example 21, but replacing TBA-CHA with ethoxycarbonyl-(OCH3)Tyr-His gave the desired compound. Mass spectrum: $(M+H)^+ = 630$.

EXAMPLE 23

Acetyl-N-methylPhe-His Amide of 2(S)-Amino-1-cyclohexyl-3(R),4(S)-dihydroxy-6-methylheptane Using the procedure of Example 21, but TBA-CHA with acetyl-N-methylPhe gave the desired compound. Mass spectrum: $M^+ = 583$.

EXAMPLE 24

Ac-Pl-His Amide of 2(S)-Amino-1-cyclohexyl-3(R),4(S)-dihydroxy-6-methylheptane Using the procedure of Example 21, but TBA-CHA with O-acetyl-L-3-phenyllactic acid (Ac-Pl-OH) gave the desired compound. HRMS calcd. for $C_{31}H_{46}N_4O_6$, (M+H) 571.3495. Found: 571.3489.

EXAMPLE 25

Pl-His Amide of 2(S)-Amino-l-cyclohexyl-3(R),4(S)-dihydroxy-6-methylheptane

The resultant compound of Example 24 (37.4 mg, 0.065 mmol) in MeOH at 0° C was treated with $K_2CO_3$ (9.1 mg, 0.065 mmol) for 30 minutes at 0° C. Evaporation provided a residue which was partitioned between ethyl acetate and water. The organic phase was washed (brine), dried ($MgSO_4$), and evaporated to give the desired compound (32 mg, 93%). Mass spectrum: $(M+H)^+ = 529$.

Anal. calcd. for $C_{31}H_{46}N_4O_6 \cdot \frac{1}{2} H_2O$: C, 64.8; H, 8.4; N, 10.4. Found: C, 64.6; H, 8.3; N, 10.1.

EXAMPLE 26

Boc-1-Nal-His Amide of 2(S)-Amino-l-cyclohexyl-3(R),4(S)-dihydroxy-6-methyl-heptane Using the procedure of Example 21, but replacing TBA-CHA with Boc-1-naphthylalanine (Boc-1-Nal) provided the desired compound. Mass spectrum: $(M+H)^+ = 678$.

EXAMPLE 27

Dba-His Amide of 2(S)-Amino-l-cyclohexyl-3(R),4(S)-dihydroxy-6-methylhectane

Using the procedure of Example 21, but TBA-CHA with 2,2-dibenzylacetic acid (Dba-OH) gave the desired compound. HRMS calcd. for $C_{36}H_{50}N_4O_4$, (M+H) 603.3910. Found: 603.3899.

EXAMPLE 28

Pp-His Amide of 2(S)-Amino-l-cyclohexyl-3(R),4(S)-dihydroxy-6-methylheptane

Using the procedure of Example 21, but TBA-CHA with 3-phenyl-propionic acid (Pp-OH) gave the desired compound. Mass spectrum: $(M+H)^+ = 513$.

Anal. calcd. for $C_{29}H_{44}N_4O_4 \cdot \frac{1}{2} H_2O$: C, 66.8; H, 8.7., N, 10.7. Found: C, 66.6; H, 8.8; N, 10.5.

EXAMPLE 29

Ethoxycarbonyl-Phe-His Amide of 2(S)-Amino-l-cyclohexyl-3(R),4(S)-dihydroxy-6-ethylheptane Using the procedure of Example 21, but replacing TBA-CHA with ethoxycarbonyl-Phe gave the desired product. Mass spectrum: $(M+H)^+ = 600$.

Anal. calcd. for $C_{32}H_{49}N_5O_6 \cdot \frac{1}{2} H_2O$: C, 63.1; H, 8.3; N, 11.5. Found: C, 62.8; H, 8.3; N, 11.4.

EXAMPLE 30

Ac-Phe-His Amide of 2(S)-Amino-1-cyclohexyl-3(R),4(S)-dihydroxy-6-methylheptane

Using the procedure of Example 21, but TBA-CHA with acetyl(Ac)-Phe gave the desired product. Mass spectrum: $(M+H)^+ = 570$.

Anal. calcd. for $C_{31}H_{47}N_5O_5 \cdot \frac{1}{2} H_2O$: C, 64.3; H, 8.2; N, 12.1. Found: C, 64.2; H, 8.3; N, 12.0.

EXAMPLE 31

Boc-Leu-His Amide of 2(S)-Amino-l-cyclohexyl-3(R),4(S)-dihydroxy-6-methylheptane Using the procedure of Example 21, but replacing TBA-CHA with Boc-Leu gave the desired product. Mass spectrum: $(M+H)^+ = 594$.

Anal. calcd. for $C_{31}H_{55}N_5O_6 \cdot \frac{1}{2} H_2O$: C, 61.8; H, 9.4; N, 11.6. Found: C, 61.8; H, 9.3; N, 11.6.

EXAMPLE 32

Tbac-Phe-His Amide of 2(S)-Amino-l-cyclohexyl-3(R),4(S)-dihydroxy-6-methylheptane Using the procedure of Example 21, but TBA-CHA with t-butyl-aminocarbonyl-Phe (Tbac-Phe) gave the desired product. Exact mass calcd for $C_{34}H_{55}N_6O_5$: 627.4233. Found: 627.4226.

EXAMPLE 33

Boc-phe-Ala Amide of 2(S)-Amino-l-cyclohexyl-3(R),4(S)-dihydroxy-6-methylheptane Using the procedure of 2, but replacing the resultant compound of Example 1 with the 3(R),4(S) diastereomer of Example 14 gave the desired compound. Mass spectrum: $(M-H)^+ = 560$.

Anal. calcd. for $C_{31}H_{51}N_3O_6$: C, 66.3; H, 9.1; N, 7.5. Found: C, 66.0; H, 9.2; N, 7.3.

EXAMPLE 34

Boc-Phe-Phe Amide of 2(S)-Amino-l-cyclohexyl-3(R),4(S)-dihYdroxy-6-methYlheptane Using the procedure of Example 33, but replacing Boc-Phe-Ala with Boc-Phe-Phe, gave the desired product. Mass spectrum: $(M+H)^+ = 638$.

Anal. calcd. for $C_{37}H_{55}N_3O_6$: C, 69.7; H, 8.7; N, 6.6. Found C, 69.4; H, 8.8; N, 6.5

EXAMPLE 35

Boc-Phe-PAla Amide of 2(S)-Amino-l-cyclohexyl-3(R),4(S)-dihydroxy-6-methylheptane Using the procedure of Example 33, but replacing Boc-Phe-Ala with Boc-Phe-(3-pyrazoyl)alanine (Boc-Phe-PAla), gave the desired compound. Mass spectrum: $(M+H)^+ = 628$.

Anal. calcd. for $C_{34}H_{53}N_5O_6 \cdot \frac{1}{2} H_2O$: C, 64.1; H, 8.5; N, 11.0. Found: C, 64 1; H, 8.3; N, 11.2.

EXAMPLE 36

Ethoxycarbonyl-phe-Leu Amide of 2(S)-Amino-cyclohexyl-3(R),4(S)-dihydroxy-6-methylheptane Using the procedure of Example 33, but Boc-Phe-Ala with Boc-Phe-Leu, gave the desired compound. Mass spectrum: $(M+H)^+ = 576$.

Anal. calcd. for $C_{32}H_{53}N_3O_6$: C, 66.7; H, 9.3; N, 7.3. Found: C, 66.4; H, 9.5; N, 7.2.

EXAMPLE 37

Boc-Phe-(SCH$_3$)Cys Amide of
2(S)-Amino-1-cyclohexyl-3(R),4(S)-dihydroxy-6-methylheptane Using the procedure of Example 33, but Boc-Phe-Ala with Boc-Phe-(SCH$_3$)Cys, gave the desired compound. Mass spectrum: $(M+H)^+ = 608$.

Anal. calcd. for C$_{32}$H$_{53}$N$_3$O$_6$S: C, 62.8; H, 8.8; N, 6.9. Found: C, 62.8; H, 8.9; N, 6.6

EXAMPLE 38

Ts-(N Me,NTMBn)-His Amide of
2(S)-Amino-1-cyclohexyl-3(R),4(S)-dihydroxy-6-methylheptane Using the procedure of Example 20, but Boc-His with (N tosyl, N methyl, N imidazole benzyl)-His [Ts-(N Me,N$_{IM}$Bn)-His] (DuVigneau, V.; Behrens, O. K. *J. Biol. Chem.* 1937, 117, 27), gave the desired compound. Mass spectrum: $(M+H)^+ = 639$.

EXAMPLE 39

Ethoxycarbonyl-Phe-MeHis Amide of
2(S)-Amino-1-clohexyl-3(R),4(S)-dihydroxy-6-methylheptane To a stirred $-78°$ C. solution of the resultant compound of Example 38 (100 mg, 0.156 mmol) in liquid NH$_3$ (5 mL) and dry tetrahydrofuran (5 mL) was added sodium until a dark green/brown color persisted for 5 minutes. Solid, powdered NH$_4$Cl was then added, and the mixture was evaporated. The residue was suspended in water and extracted several times with chloroform. The combined extracts were dried (Na$_2$SO$_4$), filtered, and evaporated to give the MeHis amide of 2(S)-amino-1-cyclohexyl-3(R),4(S)-dihydroxy-6-methylheptane.
The material was coupled to ethoxycarbonyl-Phe using to DCC/HOBT method described in Example 5 to give the desired product. Mass spectrum: $(M+H)^+ = 614$.

EXAMPLE 40

2(S)-t-Butyloxycarbonylamino-1-cyclohexyl-7-methyloct-3-ene

Using the procedure of Example 13, but replacing isopentyltriphenylphosphonium bromide with isohexyltriphenylphosphonium bromide, gave the desired product.

EXAMPLE 41

2(S)-t-Butyloxycarbonylamino-1-cyclohexyl-3(R),4(S)-dihydroxy-7-methyloctane

Using the procedure of Example 14, but replacing the resultant compound of Example 13 with the resultant compound of Example 40, gave the desired compound.

EXAMPLE 42

Boc-His Amide of
2(S)-Amino-1-cyclohexyl-3(R).4(S)-dihYdroxY-7-methYloctane

Using the procedure of Example 20, but replacing the 3(R),4(S) diastereomer of Example 14 with the resultant compound of Example 41, gave the desired product. Mass spectrum: $(M+H)^+ = 495$.

Anal. calcd. for C$_{26}$H$_{46}$N$_4$O$_5$ ¼ H$_2$O: C, 62.0; H, 9.4; N, 11.1. Found: C, 62.2; H, 9.4; N, 10.9.

EXAMPLE 43

TBA-Phe-His Amide of
2(S)-Amino-1-cyclohexyl-3(R),4(S)-dihydroxy-7-methyloctane

Using the procedure of Example 15, but replacing the resultant compound of Example 14 and Boc-Phe-His with the resultant compound of Example 42 and t-butylacetyl(TBA)-Phe gave the desired compound. Mass spectrum: $(M+H)^+ = 640$.

Anal. calcd. for C$_{36}$H$_{57}$N$_5$O$_5$ ¾ H$_2$O: C, 66.2; H, 9.0; N, 10.7. Found: C, 66.1; H, 9.1; N, 10.6.

EXAMPLE 44

2(S)-t-Butyloxycarbonylamino-1-cyclohexyl-5-methylhex-3-ene

Using the procedure of Example 13, but replacing isopentyltriphenylphosphonium bromide with isobutyltriphenylphosphonium bromide, gave the desired product. Mass spectrum: M$^+ = 295$.

Anal. calcd. for C$_{18}$H$_{33}$NO$_2$ ¼ H$_2$O: C, 72.0; H, 11.3; N, 4.7. Found: 71.7; H, 11.1; N, 4.5.

EXAMPLE 45

2(S)-t-Butyloxycarbonylamino-1-cyclohexyl-3(R).4(S)-dihydroxy-5-methylhexane

Using the procedure of Example 14, but replacing the resultant compound of Example 13 with the resultant compound of Example 44, gave the desired compound.

EXAMPLE 46

Boc-Phe-His Amide of
2(S)-Amino-1-cyclohexyl-3(R),4(S)-dihydroxy-5-methylhexane

Using the procedure of Example 15, but replacing the resultant product of Example 14 with the resultant product of Example 45, gave the desired product. Mass spectrum: $(M+H)^+ = 614$.

EXAMPLE 47

Ethoxycarbonyl-Phe-Leu Amide of
2(S)-Amino-1-cyclohexyl-3(R),4(S)-dihydroxyhexane Following the procedures used to make the resultant compound of Example 36, but replacing isopentyltriphenylphosphonium bromide with propyltriphenylphosphonium bromide, gave the desired product. Mass spectrum: M$^+ = 547$.

Anal. calcd. for C$_{30}$H$_{49}$N$_3$O$_6$ ¼ H$_2$O: C, 65.2; H, 9.0; N, 7.6. Found: C, 65.0; H, 8.9; N, 7.3.

EXAMPLE 48

Ethoxycarbonyl-Phe-Leu Amide of
2(S)-Amino-1-cyclohexyl-3(R),4(S)-dihydroxy-5-phenylpentane Following the procedures used to make the resultant compound of Example 36, but replacing isopentyltriphenylphosphonium bromide with phenethyltriphenylphosphonium bromide, gave the desired product.

EXAMPLE 49

Boc-Phe-His Amide of
2(S)-Amino-1-cyclohexyl-3(R),4(S)-dihydroxypentane

Following the procedures used to make the resultant compound of Example 15, but replacing isopentyltriphenylphos-

EXAMPLE 50

2(S)-t-Butyloxycarbonylamino-1-cyclohexyl-3(S)-hydroxyhex-5-ene

To a stirred −78° C. solution of Boc-cyclohexylalanine methyl ester (35.0 g, 123 mmol) in anhydrous toluene (200 mL) was added diisobutylaluminum hydride (140 M %, 1.5 M solution in toluene, 117 mL) at a rate to keep the internal temperature below −60° C. After stirring for an additional 20 minutes at −78° C., allyl magnesium chloride (184 mL of a 2.0 M solution in THF) was added. The mixture was allowed to stand at 0° C. for 16 hours and was then quenched with methanol. The mixture was diluted with ether and then washed seguentially with citric acid (ag) and brine. Drying (MgSO$_4$) and evaporating provided an oil which was purified by silica gel chromatography to give the desired compound in 40% yield.

EXAMPLE 51

2(S)-t-Butyloxycarbonylamino-1-cyclohexyl-3(R),4(S)-dihydroxyhex-5-ene

An allylic oxidation using stoichiometric SeO$_2$ and t-butyl hydroperoxide (Umbriet, M. A. and Sharpless, K. B. *J. Am. Chem. Soc.* 1977, 99, 5526) was performed on the resultant product of Example 50 to give the desired product after silica gel chromatography.

EXAMPLE 52

EthoxycarbonYl-Phe-Leu Amide of 2(S)-Amino-1-cyclohexyl-3(R),4(S)-dihydroxy-hex-5-ene Following the procedure of Example 15, but replacing the resultant product of Example 14 and Boc-Phe-His with the resultant product of Example 51 and ethoxycarbonyl-Phe-Leu, gave the desired product. Anal. calcd. for C$_{30}$H$_{47}$N$_3$O$_6$: C, 66.03; H, 8.68; N, 7.70. Found: C, 66.10; H, 8.83; N, 7.43.

EXAMPLE 53

(N-ButYl, 4-OCH$_3$)-Phenylalanine

To a stirred 0° C. suspension of (4-OCH3)-phenylalanine (1.00 g, 5.12 mmol) and butyraldehyde (0.406 g, 110 M %) in methanol (10 mL) was added sodium cyanoborohydride (241 mg, 75 M %). The mixture was warmed to room temperature for 23 h and filtered. The solid was washed with methanol and suction dried to give 1.07 g (83%) of the desired product. Mass spectrum: M$^+$=251. Anal. Calcd for C$_{14}$H$_{21}$NO$_3$½ H$_2$O: C, 65.3; H, 8.5; N, 5.4 Found: C, 65.1; H, 8.3; N, 5.6.

EXAMPLE 54

(N-Butyl, 4-OCH$_3$)Phe-His Amide of 2(S)-Amino-1-cyclohexyl-3(R),4(S)-dihydroxy-6-methylheptane.

Using the procedure of Example 21, but replacing TBA-CHA with the resultant product of Example 53 gave the desired compound. Mass spectrum: (M+H)$^+$=614. Anal. Calcd for C$_{34}$H$_{55}$N$_5$O$_5$½ H$_2$O: C, 65.6; H, 9.1; N, 11.2. Found: C, 65.3; H, 9.0; N, 11.3.

EXAMPLE 55

H-(4-OCH$_3$)Phe-Leu Amide of 2(S)-Amino-1-cyclohexyl-3(R),4(S)-dihydroxy-6-methylheptane.

Using the procedure of Example 33, but replacing Boc-Phe-Ala with Cbz-(3-I,4- QCH$_3$)Phe-Leu provided the protected iodinated product. Deprotection and deiodination was achieved by hydrogenating 0.59 g in methanol (150 mL) with NaOAc 3H$_2$O (0.40 g), 2.5% Rh/BaSO$_4$ (1.5 g), 20% Pd/C (0.29 g) at 4 atmospheres H$_2$ for 2.5 h. Filtration and evaporation provided a residue which was partitioned between ethyl acetate and sat. aq. NaHCO$_3$ The organic layer was washed with dilute Na$_2$S$_2$O$_3$ and brine, dried, filtered, and evaporated to give a solid. Recrystallization from CH$_2$Cl$_2$/hexane provided 260 mg (65%) of the desired compound. HRMS: M$^+$ Calcd for C$_{30}$H$_{52}$N$_3$O$_5$: 534.3907. Measured: 534.3925.

EXAMPLE 56

(N,N-Dimethyl,4-methoxy)-Phe-Leu Amide of 2(S)-Amino-1-cyclohexyl-3(R),4(S)-dihydroxy-6-methylheptane.

The resultant product of Example 55 (130 mg, 0.243 mmol) was hydrogenated (1 atmosphere H ) with 10% Pd/C (39 mg) in methanol/formalin (12 mL/5 mL) for 8 h. filtering and evaporating (high vacuum) provided a residue which was chromatographed on silica gel to give 43 mg (32%) of the desired compound. HRMS: (M+H)$^+$ calculated for C$_{32}$H$_{56}$N$_3$O$_5$: 562.4220. Measured: 562:4230.

EXAMPLE 57

H-Phe-Leu Amide of 2(S)-Amino-1-cyclohexyl-3(R),4(S)-dihydroxY-6-methylheptane.

Following the procedure of Example 55, but replacing Cbz-(3-I,4-OCH3)Phe-Leu with Cbz-Phe-Leu and omitting NaOAc.3H$_3$O and 2.5% Rh/BaSO$_4$ in the reduction step, provided the desired compound. Mass spectrum: (M+H)$^+$=504. Anal. Calcd for C$_{29}$H$_{49}$N$_3$O$_4$: C, 69.1; H, 9.8; N, 8.3. Found: C, 69.0; H, 10.1; N, 8.3.

EXAMPLE 58

[N-(2-Cyanoethyl)]Phe-Leu Amide of 2(S)-Amino-1-cyclohexyl-3(R),4(S)-dihydroxy-6-methylheptane.

A suspension of the resultant compound of Example 57 (297 mg, 0.590 mmol) in acrylonitrile (2 mL) was refluxed for 3 days. Evaporation provided a residue which was dissolved in ethyl acetate, filtered, evaporated and chromatographed on silica (dichloromethane/methanol, 97.5/2.5) to give 162 mg (49%) of the desired compound. Mass spectrum: (M+H)$^+$=557. Anal. Calcd for C$_{32}$N$_{52}$N$_4$O$_4$: C, 69.0; H, 9.4; N, 10.1. Found: C, 68.6; H, 9.5; N, 9.9.

EXAMPLE 59

[N-(3-Aminopropyl)]Phe-Leu Amide of 2(S)-Amino-1-cyclohexyl-3(R),4(S)-dihydroxy-6-methylheptane.

The resultant compound of Example 58 (75 mg, 0.135 mmol) was hydrogenated (4 atmospheres H$_2$) over Raney Nickel (85 mg) in anhydrous methanol/ammonia (20 mL/5 mL) for 3 h. Filtration and evaporation provided the desired product (68 mg). Mass spectrum: $(M+H)^+ = 561$.

EXAMPLE 60

(N,N-Dimethyl)Gly-Phe-His Amide of 2(S)-Amino-1-cyclohexy 1-3(R),4(S)-dihydroxy-6-methylheptane.

Using the procedure of Example 56, but replacing the resultant product of Example 55 with the resultant product of Example 64, gave the desired product. Mass spectrum: $(M+H)^+ = 613$.

EXAMPLE 61

Cbz-β-Ala-Phe-His Amide of 2(S)-Amino-1-cyclohexyl-3(R),4(S)-dihydroxy-6-methylheptane.

Using the procedure of Example 21, but replacing TBA-CHA with Cbz-B-Ala-Phe gave the desired compound. Mass spectrum: $(M+H)^+ = 733$. Analysis calculated for $C_{40}H_{56}N_6O_7$: C, 65.6; H, 7.7; N, 11.5. Found: C, 65.2; H, 7.7; N, 11.2.

EXAMPLE 62

H-β-Ala-Phe-His Amide of 2(S)-Amino-1-cyclohexyl-3(R), 4(S)-dihydroxy-6-methylheptane Diacetic Acid Salt.

The resultant compound of Example 61 (1.00 g, 1.36 mmol) in acetic acid (14 mL) was hydrogenated at 1 atmosphere with 10% Pd/C (0.50 g) for 3 h. Filtration, extraction of the catalyst with acetic acid, and evaporation of the combined acetic acid solutions gave a residue which was dissolved in water (25 mL) and lyopholized to provide 891 mg (91%) of the desired product. Mass spectrum: $(M+H)^+ = 599$ (free base). Analysis Calculated for $C_{36}H_{58}N_6O_{9\frac{1}{2}}$ $H_2O$: C, 59.4; H, 8.1; N, 11.5. Found: C, 59.3., H, 8.0; N, 11.2.

EXAMPLE 63

Cbz-Sar-phe-His Amide of 2(S)-Amino-1-cyclohexyl-3(R),4(S)-dihydroxy-6-methylheptane.

Using the procedure of Example 21, but replacing TBA-CHA with Cbz-Sar-Phe gave the desired compound. Mass spectrum: $(M+H)^+ = 733$. Anal. Calcd for C, 64.8; H, 7.7; N, 11.3. Found: 65.0; H, 7.6; N, 11.3.

EXAMPLE 64

H-Sar-Phe-His Amide of 2(S)-Amino-1-cyclohexyl-3(R),4(S)-dihydroxy-6-methylheptane Diacetic Acid Salt.

Using the procedure of Example 62, but replacing the resultant compound of Example 61 with the resultant compound of Example 63 gave the desired product. Mass spectrum: $(M+H)^+ = 599$ (free base). Anal. calcd for $C_{36}H_{58}N_6O_9H_2O$: C, 58.7; H, 8.2; N, 11.4. Found: 58.5; H, 8.1; N, 11.4.

EXAMPLE 65

Cbz-GABA-Phe-His Amide of 2(S)-Amino-1-cyclohexyl-3(R), 4(S)-dihydroxy-6-methylheptane.

Using the procedure of Example 21, but relacing TBA-CHA with Cbz-GABA-Phe (GABA is 4-aminobutyric acid) gave the desired compound.

EXAMPLE 66

H-GABA Phe-His Amide of 2(S)-Amino-1-cyclohexyl-3(R), 4(S)-dihydroxy-6-methyl-heptane Diacetic Acid Salt.

Using the procedure of Example 62, but replacing the resultant compound of Example 61 with the resultant compound of Example 65 gave the desired product.

EXAMPLE 67

Cbz-Isonipectoyl-Phe-His Amide of 2(S)-Amino-1-cyclohexyl-3(R),4(S)-dihydroxy-6-methylheptane.

Using the procedure of Example 21, but replacing TBA-CHA with Cbz-Isonipectoyl-Phe gave the desired compound. Mass spectrum: $(M+H)^+ = 773$. Analysis calculated for $C_{43}H_{60}N_6O_7$ $H_2O$: C, 65.3; H, 7.9; N, 10.6. Found: 65.4; H, 7.6; H, 10.5.

EXAMPLE 68

H-Isonipectoyl-Phe-His Amide of 2(S)-Amino-1-cyclohexyl-3(R),4(S)-dihydroxy-6-methylheptane Diacetic Acid Salt.

Using the procedure of Example 62, but replacing the resultant compound of Example 61 with the resultant compound of Example 67 gave the desired product. Mass spectrum: $(M+H)^+ = 639$ (free base).

EXAMPLE 69

Cbz-D-Ala-Phe-His Amide of 2(S)-Amino-1-cyclohexyl-3(R), 4(S)-dihydroxy-6-methylheptane.

Using the procedure of Example 21, but replacing TBA-CHA with Cbz-D-Ala-Phe gave the desired compound. Mass spectrum: $(M+H)^+ = 733$. Analysis calculated for $C_{40}H_{56}N_6O_7$ 1.5 $H_2O$: C, 63.2; H, 7.8; N, 11.0. Found: C, 63.0; H, 7.4; N, 11.0.

EXAMPLE 70

H-D-Ala-Phe-His Amide of 2(S)-Amino-1-cyclohexyl-3(R), 4(S)-dihydroxy-6-methylheptane Diacetic Acid Salt.

Using the procedure of Example 62, but replacing the resultant compound of Example 61 with the resultant compound of Example 69 gave the desired product. Mass spectrum: $(M+H)^+ = 599$ (free base).

EXAMPLE 71

3-Benzyloxycarbonylamino-3-methylbutanoic Acid.

A solution of 2,2-dimethyl-3-carbomethyoxypropionic acid [LeMaul, Bull. Soc. Chim. Fr., 828 (1965), 20 g, 0.125 mol], diphenylphosphorylazide (34.3 g. 0.125 mol) and triethylamine was heated in toluene (150 mL) at 100° C. for 2 h. After cooling to 5° C, the toluene solution was washed successively with 0.5 M HCl, aqueous NaHCO3 and brine. Evaporation of the dried solution gave a residue which was chromatographed on silica gel eluting with 60/40 hexane- ether. There was obtained 13 g of methyl 3-isocyanato-3-methylbutanoate as a mobile liquid. A solution of this material in toluene (20 mL) was treated with benzyl alcohol (13 mL) and the resulting mixture heated at reflux for 40 h. Evaporation of the toluene left a residue which was dissolved in methanol (125 mL) and then treated with a solution of NaOH (6.6 g, 0.165 mol) in 22 mL of water.

After 5 h, the reaction mixture was partially evaporated, washed with ether and acidified with 6N HCl. Extraction with methylene chloride and evaporation gave 21 g of the desired product NMR (300 MHz, CDCl$_3$) 1.42 (s, 6H), 2.78 (s, 2H), 5.08 (s, 2H).

EXAMPLE 72

Cbz-[$\beta,\beta$-di-Me)-$\beta$-Ala]-Phe-OCH$_3$.

A 4.0 g sample of 3-benzyloxycarbonylamino-3-methylbutanoic acid was coupled to phenylalanine methyl ester hydrochloride (3.43 g) using the mixed anhydride procedure described in Example 2. Purification of the crude product by flash chromatography eluting with 65/35 ether-hexane gave an 86% yield of product. NMR (300 MHz, CDCl$_3$) 1.32 (s, 3H), 1.34 (s, 3H), 2.46 (d, 1H), 2.63 (d, 1H), 2.98 (dd, 1H), 3.09 (dd, 1H), 3.70 (s, 3H), 4.86 (dd, 1H), 4.97 (d, 1H), 5.2 (d, 1H), 5.3 (s, 1H), 6.13 (d, 1H).

EXAMPLE 73

Cbz-[$\beta,\beta$-di-Me)-$\beta$-Ala]-Phe-OH

To a 0° C. solution of Cbz-[($\beta,\beta$-di-Me)-$\beta$-Ala]-Phe-OMe (1.5 g, 3.63 mmol) in dioxane (15 mL) was added a solution of lithium hydroxide (0.174 g, 4.15 mmol) in water (7.5 mL). After stirring for 1 h at 0°–5° C., the reaction mixture was diluted with cold water and extracted 2× with ether. The aqueous portion was acidified with 6N HCl and extracted with ether. The organic extract was washed with brine and evaporated to give an 87% yield of product as a viscous liquid.

EXAMPLE 74

Cbz-[($\beta,\beta$-di-Me)-$\beta$-Ala]-Phe-His Amide of 2(S)-Amino-1-cyclohexyl-3(R),4(S)-dihydroxy-6-methylheptane.

Using the procedure of Example 21, but replacing TBA-CHA with Cbz-[($\beta,\beta$-di-Me)-$\beta$-Ala]-Phe gave the desired compound. Mass spectrum: (M+H)+ =761. Anal. Calcd for C$_{42}$H$_{60}$N$_6$O$_7$ ½ H$_2$O: C, 65.5; H, 8.0; N, 10.9. Found: C, 65.6; H, 7.9; N, 11 0.

EXAMPLE 75

H-[($\beta,\beta$-di-Me)-$\beta$-Ala]-Phe-His Amide of 2(S)-Amino-1-cyclohexyl-3(R),4(S)-dihydroxy-6-methylheptane Diacetic Acid Salt.

Using the procedure of Example 62, but replacing the resultant compound of Example 61 with the resultant compound of Example 74 gave the desired product. Mass spectrum: (M+H)+ =627 (free base). Anal. Calcd for C$_{38}$H$_{62}$N$_6$O$_9$ H$_2$O: C, 59.7; H, 8.4; N, 11.0. Found: C, 59.5; H, 8.4; N, 11.3.

EXAMPLE 76

Cbz-Pro-Phe-His Amide of 2(S)-Amino-1-cyclohexyl-3(R), 4(S)-dihydroxy-6-methyl- heptane.

Using the procedure of Example 21, but replacing TBA-CHA with Cbz-Pro-Phe gave the desired compound. Mass spectrum: (M+H)+ =759. Analysis calculated for C$_{42}$H$_{58}$N$_6$O$_7$ ½ H$_2$O: C, 65.7, H, 7.7; N, 10.9. Found: 65.7, H, 7.7; N, 10.9.

EXAMPLE 77

H-Pro-Phe-His Amide of 2(S)-Amino-1-cyclohexyl-3(R), 4(S)-dihydroxy-6-methylheptane Acetic Acid Salt.

Using the procedure of Example 62, but replacing the resultant compound of Example 61 with the resultant compound of Example 76 gave the diacetic acid salt as a tacky solid. A portion of the di-salt was partioned betwen satd. NaHCO$_3$ and dichloromethane. The aqueous layer was further extracted with dichloromethane and the combined organic layers were dried, filtered and evaporated to give the desired product. Mass spectrum: (M+H)+ =625 (free base). Analysis calculated for C$_{36}$H$_{56}$N$_6$O$_7$ 2 H$_2$O: C, 60.0; H, 8.4; N, 11.6. Found: C, 59.9; H, 7.9; N, 11.5.

EXAMPLE 78

3-Benzyloxycarbonylamino-2,2-dimethylpropionic Acid.

3-Carbomethoxy-3-methylbutanoic acid [Bull. Soc. Chim. Fr., 828 (1965), 7.85 g, 0.049 mol] was reacted with diphenylphosphorylazide and triethylamine as described in Example 71. After heating the toluene solution for 1.5 h, benzyl alcohol (8 g) was added directly to the reaction mixture and heating at reflux was continued for 20 h. Work-up and purification as in Example 71 gave methyl 3-benzyloxycarbonylamino-2,2-dimethylpropionate. NMR (300 MHz, CDCl$_3$): 1.2 (s, 6H), 3.3 (d, 2H), 3.68 (s, 3H), 5.1 (s, 2H), 5.22 (m, 1H). A sample of the methyl ester (6.21 g, 0.023 mol) was saponified with 3.1 g (0.78 mol) of NaOH in 100 mL ethanol/10 mL H2O at room temperature for 48 h. Work-up as in Example 71 gave the desired product as a liquid. NMR (300 MHz, CDCl$_3$): 1.23 (s. 6H), 3.32 (d, 2H), 5.10 (s, 2H), 5.27 (m, 1H).

EXAMPLE 79

Cbz-[($\beta,\beta$-di-Me)-$\beta$-Ala]-Phe-OCH$_3$.

To a solution of 3-benzyloxycarbonylamino-2,2-dimethylpropionic acid (1.5 g, 5.97 mmol) in methylene chloride (13 mL) was added oxalyl chloride (0 757 g, 5.97 mmol) and dimethylformamide (30 µl). After stirring for 1 h at room temperature, the reaction mixture was cooled to 0° C. and treated successively with phenylalanine methyl ester hydrochloride (1.29 g, 5.97 mmol) and N-methylmorpholine (1.81 g, 17.9 mmol). Stirring for 1 h at 0°–5° C. was followed by distribution between CH$_2$Cl$_2$ and 0.5 N HCl. The organic phase was washed with aqueous NaHCO$_3$ and brine and dried over MgSO$_4$ Evaporation of the solvent gave a residue which was purified by chromatography. There was obtained a 69% yield of product as a liquid. NMR (300 MHz, CDCl$_3$): 1.11 (s, 3H), 1.12 (s, 3H), 3.05 (dd, 1H), 3.18 (dd, 1H). 3.23 (d, 1H), 3.24 (d, 1H), 3.75 (s, 3H); 4.82 (dd, 1H), 5.08 (s, 2H), 5.37 (broad t, 1H), 6.04 (d, 1H).

EXAMPLE 80

Cbz-[($\beta,\beta$-di-Me)-$\beta$-Ala]-Phe-OH.

The hydrolysis of the methyl ester was carried out by the procedure described in Example 71 to give the desired product in 90% yield as a viscous liquid.

EXAMPLE 81

Cbz-[β,β-di-Me)-β-Ala]-Phe-His Amide of 2(S)-Amino-1-cyclohexyl-3(R),4(S)-dihydroxy-6-methylheptane.

Using the procedure of Example 21, but replacing TBA-CHA with Cbz-[(β,β-di-Me)-β-Ala]-Phe gave the desired compound. Mass spectrum: $(M+H)^+ = 761$.

EXAMPLE 82

[(β,β-Di-Me)-β-Ala]-Phe-His Amide of 2(S)-Amino-1-cyclohexyl-3(R),4(S)-dihydroxy-6-methylheptane Bis acetic acid salt.

Using the compound from Example 81 and the procedure of Example 62 gave the desired product in 71% yield. Mass spectrum: $(M+H)^+ = 627$.

EXAMPLE 83

Cbz-Phe-His Amide of 2(S)-Amino-1-cyclohexyl-3(R),4(S)-dihydroxy-6-methylheptane Using the procedure of Example 21 but replacing TBA-CHA with Cbz-Phe gave the desired compound. Mass spectrum: $(M+H)^+ = 661$.

EXAMPLE 84

Phe-His Amide of 2(S)-Amino-1-cyclohexyl-3(R),4(S)-dihydroxy-6-methylheptane.

A solution of the product from Example 83 (180 mg, 0.273 mmol) in methanol (50 mL) was hydrogenolyzed in a Parr Apparatus with 90 mg of 20% Pd/C and 4 atmospheres of hydrogen. After the hydrogen uptake ceased, the catalyst was filtered and the filtrate evaporated to the desired product (90 mg, 63%). Mass spectrum: $(M+H)^+ = 527$.

EXAMPLE 85 alpha-Aminoisobutyryl-Phe-His Amide of 2(S)-Amino-1-cyclohexyl-3(R),4(S)-dihydroxy-6-methylheptane.

A mixture of alpha-aminoisobutyric acid N-carboxy anhydride (10.9 mg, 0.085 mmol) and the product from Example 84 (44.6 mg, 0.085 mmol) in dimethylformamide (3 mL) was stirred at room temperature for 16 h. The dimethyl- formamide was evaporated in vacuo and the residue was distributed between chloroform and water. The organic phase was dried and evaporated to a residue which was chromatographed on silica gel eluting with methanol-chloroform mixtures. There was obtained 35 mg (68%) of the desired product. Mass spectrum: $(M+H)^+ = 612$.

EXAMPLE 86

(Pyridin-3-yl-sulfonyl)-phe-His Amide of 2(S)-Amino-1-cyclohexyl-3(R),4(S)-dihydroxy-6-methylheptane.

Using the procedure of Example 21, but replacing TBA-CHA with (pyridin-3-yl-sulfonyl)-Phe gave the desired product.

EXAMPLE 87

(Pyrazin-2-yl-carbonyl)-Phe-His Amide of 2(S)-Amino-1-cyclohexyl-3(R),4(S)-dihydroxy-6-methylheptane.

Using the procedure of Example 21, but replacing TBA-CHA with (pyrazin-2-yl-carbonyl)-Phe gave the desired product. Mass spectrum: $(M+H)^+ = 634$. Anal. Calcd for $C_{34}H_{47}N_7O_5 \cdot \frac{1}{4} H_2O$: C, 64.0; H, 7.5; N, 15.4. Found: C, 63.9; H, 7.6; N, 15.2.

EXAMPLE 88

(Imidazol-4-yl-acetyl)-Phe-Leu Amide of 2(S)-Amino-1-cyclohexyl-3(R),4(S)-dihydroxy-6-methylheptane.

Using the coupling conditions of Example 21 with 4-imidazoleacetic acid and the resultant product of Example 57 provided the desired product. Mass spectrum: $(M+H)^+ = 612$. Analysis calculated for $C_{34}H_{53}N_5O_5 \cdot \frac{1}{2} H_2O$: C, 65.9; H, 8.9; N, 11.3. Found: C, 65.9; H, 8.9; N, 11.3

EXAMPLE 89

(Pyrrol-2-yl-carbonyl)-Phe-His Amide of 2(S)-Amino-1-cyclohexyl-3(R),4(S)-dihydroxy-6-methylheptane.

Using the procedure of Example 21, but replacing TBA-CHA with (pyrrol-2-yl-carbonyl)-Phe gave the desired product. Mass spectrum: $(M+H)^+ = 621$.

EXAMPLE 90

Allyloxycarbonyl-Phe-Leu Amide of 2(S)-Amino-1-cyclohexyl -3(R),4(S)-dihydroxy-6-methylheptaine.

Using the procedure of Example 33, but replacing Boc-Phe-Ala with allyloxy carbonyl-Phe-Leu provided the desired product. Mass spectrum: $(M+H)^+ = 588$. Anal. Calcd for $C_{33}H_{53}N_3O_6$: C, 67.4; H, 9.1; N, 7.2. Found: C, 67.6; H, 9.0; N, 7.1.

EXAMPLE 91

3-Hydroxypropyloxycarbonyl-Phe-Leu Amide of 2(S)-Amino-1-cyclohexyl-3(R),4(S)-dihydroxy-6-methylheptane.

To a stirred 0° C solution of the resultant compound of Example 90 (1.25 g, 2.13 mmol) in dry tetrahydrofuran (THF, 50 mL) was added 9-borabicyclo[3.3.1]- nonane (9-BBN, 25.5 mL of a 0.5M solution in THF). The mixture was warmed to room temperature for 12 h and then cooled to 0° C. Water (15 mL) and 3M NaOH (4.5 mL) were added followed 2 min later by 30% $H_2O_2$ (5 mL). The mixture was partitioned between brine (20 mL) and ethyl acetate (100 mL). The organic phase was washed (brine), dried ($Na_2SO_4$), filtered, and evaporated to a thick oil. Recrystallization twice (dichloromethane/ether) provided 670 mg (52%) of the desired compound. Mass spectrum: $(M+H)^+ = 605$. Analysis calculated for $CC_{33}H_{55}N_3O_7$: C, 65.4; H, 9.2; N, 6.9. Found: C, 65.4; H, 9.1; N, 6.8.

EXAMPLE 92

Cbz-Gly Ester of the Resultant Compound of Example 91 (at 3-Hydroxypropyloxy Group).

To a stirred 0° C. suspension of the resultant compound of Example 91 (60 mg. 0.099 mol), Cbz-Gly-OH (20.7 mg, 0.099 mmol), and 4-dimethylaminopyridine (60 mg, 0 495 mmol) in dichloromethane (10 mL) was added ethyldimethylaminopropyl carbodiimide hydrochloride (38 mg, 0.198 mmol). The mixture was warmed at room temperature for 15 h and then diluted with dichloromethane and washed seguentially with 1M $H_3PO_4$, satd $NaHCO_{33}$ and brine. Drying ($Na_2SO_4$), filtering, and evaporating provided 57 mg (72%) of the desired compound. Mass spectrum: $(M+H)^+ = 797$.

EXAMPLE 93

H-Gly-Ester of the Resultant Compound of Example 91 (at 3-Hydroxypropyloxy Group).

The resultant compound of Example 92 (13 mg, 0.016 mmol) was hydrogenated (1 atmosphere $H_2$) with 10% Pd/C (4 mg) in methanol for 3 h. Filtration, evaporation and chromatography on silica (dichloromethane/methanol, 95/5–90/10) provided 4 mg (37%) of the desired product. HRMS: $(M+H)^+$ calcd for $C_{35}H_{58}N_4O_8$: 663.4333. Found: 663.4355.

EXAMPLE 94

Lysine Ester of the Resultant Compound of Example 91 (at 3-Hydroxypropyloxy Group) Diacetic Acid Salt.

Following the procedure of Example 92 but replacing Cbz-Gly-OH with a,e-di- Cbz-Lys-OH provide the desired protected peptide. Hydrogenation according to the procedure of Example 93, but replacing methanol with acetic acid provide the desired compound.

EXAMPLE 95

Hemisuccinate Ester of the Resultant Compound of Example 91 (at 3-Hydroxypropyloxy Group).

Using the procedure of Example 92, but replacing Cbz-Gly with benzyl succinate provided the protected product Deprotection was achieved by following the procedure of Example 103 to give the desired product.

EXAMPLE 96

Phosphate Ester of the Resultant Compound of Example 91 (at 3-Hydroxypropyloxy Group).

Using the procedure of Example 92, but replacing Cbz-Gly with dibenzylphosphate provided the protected product Deprotection was achieved by following the procedure of Example 103 to give the desired product.

EXAMPLE 97

2(R,S),3-Dihydroxypropyloxycarbonyl-Phe-Leu Amide of 2(S) -Amino-1-cyclohexyl-3(R),4(S)-dihydroxy-6-methylheptane.

Following the procedure of Example 14, but replacing the resultant compound of Example 13 with the resultant compound of Example 90, and heating the mixture at 50° C. for 24 h, gave the desired product Mass spectrum $(M+H)^+ = 622$. Anal. Calcd for $C_{33}H_{55}N_3O_8$ ½ $H_2O$: C, 62.8; H, 8.9; N, 6.7. Found: C, 63.0; H, 8.6; N, 6.7.

EXAMPLE 98

Cbz-Gly Mono- and Diesters of the Resultant Compound of Example 97 (at the 3-Hydroxypropyloxy and 2, 3-Dihydroxypropyl Groups, Respectively).

Using the procedure of Example 92, but replacing the resultant compound of Example 91 with the resultant compound of Example 97, provided a mixture of the desired mono- and diesters Separation was achieved by silica gel chromatography.

EXAMPLE 99

H-Gly-Ester of the Resultant Compound of Example 97 (at the 3-Hydroxypropyl Group) Acetic Acid Salt.

Using the procedure of Example 93, but replacing the resultant compound of Example 92 with the resultant monoester of Example 98 and replacing methanol with acetic acid, gave the desired product.

EXAMPLE 100

H-Gly-Diester of the Resultant Compound of Example 97 (at the 2,3-Dihydroxypropyl Group) Diacetic Acid Salt Using the procedure of Example 93, but replacing the resultant compound of Example 92 with the resultant diester of Example 98 and replacing methanol with acetic acid, provided the desired compound.

EXAMPLE 101

Ethoxycarbonyl-(OBn)Thr-His Amide of 2(S)-Amino-1-cyclohexyl-3(R),4(S)-dihydroxy-6-methylhexane.

Using the procedure of Example 21, but replacing TBA-CHA with ethoxycarbonyl-threonine benzyl ether [(OBn)Thr] gave the desired compound Mass spectrum: $(M+H)^+ = 16$. Anal Calcd for $C_{32}H_{49}N_5O_7$: C, 62.4; H, 8.0; N, 11.4. Found: 62.3; H, 8.0; N, 11.3.

EXAMPLE 1-2

Benzyloxyacetyl-Phe-His Amide of 2(S)-Amino-1-cyclohexyl-3(R),4(S)-dihydroxy-6-methylheptane.

Using the procedure of Example 21, but replacing TBA-CHA with benzyloxyacetyl-Phe gave the desired compound. Mass spectrum: $(M+H)^+ = 676$. Analysis calculated for $C_{38}H_{53}N_5O_6$ ¼ $H_2O$: C, 67.1; H, 7.9; N, 10.3. Found: 67.0; H, 7.9; N, 10.2.

EXAMPLE 103

Hydroxyacetyl-Phe-His Amide of 2(S)-Amino-1-cyclohexyl-3(R),4(S)-dihydroxy-6-methylheptane.

The resultant compound of Example 102 (250 mg, 0.370 mmol) in acetic acid (3.7 mL) was hydrogenated at 1 atmosphere $H_2$ with 10% Pd/C (125 mg) for 23 h. Filtration, extraction of the catalyst with acetic acid, and evaporation of the combined acetic acid solutions gave a residue which was partitioned between ethyl acetate and satd. aq. $NaHCO_3$. Exhaustive extraction of the aqueous phase with ethyl acetate, combination of all organic layers, and evaporation provided crude product which was recrystallized (ethylacetate/methanol/methylcyclohexane) to give 157 mg (72%) of the desired product. Mass spectrum: $(M+H)^+ = 586$. Anal. Calcd for $C_3H_{47}N_5O_6$ $H_2O$: C, 61.7; H, 8.2; N, 11.6. Found: C, 62.1; H, 8.1; N, 11.4.

EXAMPLE 104

Acetyl-8-Ala-Phe-His Amide of 2(S)-Amino-1-cyclohexyl-3(R),4(S)-dihydroxy-6-methylheptane.

Using the procedure of Example 21, but replacing TBA-CHA with Acetyl-8-Ala-Phe provided the entire compound.

EXAMPLE 105 i-Bu-Pl-His Amide of 2(S)-Amino-l-cyclohexyl-3(R),4(S)-dihydroxy-6-methylheptane.

Using the procedure of Example 21, but replacing TBA-CHA with 0-isobutyl-L-3-phenyllactic acid (i-Bu-Pl-OH) gave the desired compound.

EXAMPLE 106

Isobutyryl-Homo-Phe methyl ester

To a suspension of (+)alpha-amino-4-phenylbutyric acid (Homo-Phe) methyl ester hydrochloride (0.83 g, 3.61 mmol) in methylene chloride cooled in an ice bath was added successively isobutyric anhydride (0.57 g, 3.61 mol) and N-methylmorpholine (0.79 mL, 7.22 mmol). After stirring for 30 min at 0°–5° C., the reaction mixture was distributed between methylene chloride and 0.5N HCl. The organic layer was washed with aqueous NaHCO$_3$ and brine solution and then dried over MgSO$_4$. Evaporation of the solvent gave a solid residue which was triturated with hexane to provide 700 mg of product, mp 72°–73°.

EXAMPLE 107

Isobutyryl-Homo-Phe

The hydrolysis of the methyl ester was carried out by the procedure described in Example 73 to give the desired product in 90% yield.

EXAMPLE 108

Isobutyryl-Homo-Phe-His Amide of 2(S)-Amino-l-cyclohexyl-3(R),4(S)-dihydroxy-6-methylheptane.

Using the procedure of Example 21, but replacing TBA-CHA with isobutyryl-homo- Phe gave the desired compound. Mass spectrum: (M+H)$^+$=612.

EXAMPLE 109

2(S)-[[(4-Morpholinyl)carbonyl]oxy]-3-phenylpropionic acid methyl ester.

To L-phenyllactic acid methyl ester (3.2 g) was added 150 mL of 12.5% phosgene in toluene and 25 drops of dimethylformamide. After stirring for 16 h at room temperature, the solvent was evaporated and the residue chased several times with benzene. The resulting product was dissolved in methylene chloride (50 mL), cooled to 0° C. and treated by dropwise addition with 3.86 g (0.044 mol) of morpholine. The reaction mixture was stirred for 2 h at 0°–5° C. and then distributed between 0.5N HCl and methylene chloride. The organic phase was washed with aqueous NaHCO$_3$ and brine and evaporated to a residue. Flash chromatography on silica gel eluting with 2/1 ether-hexane gave a 65% yield of product. NMR (300 MHZ): 3.08 (dd, 1H), 3.20 (dd, 1H), 3.8 (s, 3H), 5.19 (dd, 1H).

EXAMPLE 110

2(S)-[(4-Morpholinyl)carbonyl]oxy-3-phenylpropionic acid.

Using the hydrolysis procedure of Example 73, the title compound was obtained in 90% yield.

EXAMPLE 111

2(S)-[(4-Morpholinyl)carbonyl]oxy-3-phenylpropionyl-His Amide of 2(S)-Amino-l-cyclohexyl-3(R),4(S)-dihydroxy-6-methylheptane.

Using the procedure of Example 21, put replacing TBA-CHA with the product from Example 110, gave the desired product in 60% yield. Mass spectrum: (M+H)$^+$=642.

EXAMPLE 112

2(S)-[[(4-Cbz-l-Piperazinyl)carbonyl]oxy]-3-phenylpropionic acid methyl ester.

Using the procedure of Example 109, but replacing morpholine with Cbz- piperazine, gave the desired product in 63% yield.

EXAMPLE 113

2(S)-[[(4-Cbz-l-Piperazinyl)carbonyl]oxy])-3-phenylpropionic acid.

Using the hydrolysis procedure of Example 73 gave the desired product in 93% yield.

EXAMPLE 114

2(S)-[[(4-Cbz-1-Piperazinyl)carbonyl]oxy]-3-phenylpropionyl-Phe-His Amide of 2(S)-Amino-1-cyclohexyl-3(R),4(S)-dihydroxy-6-methylheptane.

Using the procedure of Example 21, but replacing TBA-CHA with the resultant compound from Example 113, gave the title compound. Mass spectrum: (M+H)$^+$=775.

EXAMPLE 115

2(S)-[[(1-Piperazinyl)carbonyl]oxy]-3-phenylpropionyl-Phe-His Amide of 2(S)-Amino-1-cyclohexyl-3(R),4(S)-dihydroxy-6-methylheptane.

Using the procedure of Example 62 gave the title compound in 85% yield. M.p. 158°–160° C.

EXAMPLE 116

[(4-Morpholinyl)carbonyl]-Phe methyl ester.

A suspension of L-phenylalanine methyl ester hydrochloride (6 g) in toluene (125 mL) was heated to 100° C. while phosgene gas was bubbled into the reaction mixture After approximately 1-½-2 h, the mixture became homogeneous. The passage of phosgene was continued for an additional 15 min, keeping the temperature at 90°14 100° C. The toluene was then evaporated and the residue chased several times with benzene A 6.5 g (0.03167 mol) sample of a-isocyanato-L-phenyl-alanine methyl ester was dissolved in 50 mL of methylene chloride and cooled to 0° C. Morpholine (2.76 mL, 0.03167 mol) dissolved in 5 mL of methylene chloride was added dropwise. After 10 min at 0°–5° C., the reaction mixture was distributed between 0 5N HCl and methylene chloride. The organic layer was washed with aqueous NaHCO$_3$ and dried over MgSO$_4$. Evaporation of the solvent gave 7 g of product after trituration with hexane, mp 90°–91°.

EXAMPLE 117

[(4-Morpholinyl)carbonyl]-Phe

Using the procedure of Example 73 gave the title compound in 89% yield.

EXAMPLE 118

[(4-Morpholinyl)carbonyl]-phe-His Amide of 2(S)-Amino-1-cyclohexyl-3(R),4(S)-dihydroxy-6-methylheptane.

Using the procedure of Example 2I, but replacing TBA-CBA with [(4-morpholinyl)carbonyl]-Phe, gave the desired compound Mass spectrum $(M+H)^+ = 641$.

EXAMPLE 119

(Dimethylamino)carbonyl]-Phe-His Amide of 2(S)-Amino-1-cyclohexyl-3(R) 4(S)-dihydroxy-6-methylheptane.

Using the procedures of Examples 116, 73, and 21, this compound was prepared. Mass spectrum: $(M+H)^+ = 599$.

EXAMPLE 120

[[Methyl-(2-hydroxyethyl)amino]carbonyl]-Phe-His Amide of 2(S)-Amino-1-cycloboxyl-3(R),4(S)-dihydroxy-6-methylheptane.

Using the procedures of Examples 116, 73, and 21, the title compound was synthesized. Anal. calcd for $C_{32}H_{52}N_6O_6 \cdot 1\frac{1}{2} H_2O$: C, 60.44; H, 8.45; N, 12.82. Found: C, 60.36: H. 8.11; N. 12.77.

EXAMPLE 121

[(1-Cbz-4-Piperazinyl)carbonyl]-Phe methyl ester.

Using the procedure of Example 116, but replacing morpholine with 1-Cbz-piperazine, gave the desired product, mp 114°–115°.

EXAMPLE 122

[(1-Cbz-4-Piperazinyl)carbonyl]-Phe

Using the procedure of Example 73 gave the desired product in 89% yield.

EXAMPLE 123

[(1-Cbz-4-Piperazinyl)carbonyl]-Phe-His Amide of 2(S)-Amino-1-cyclohexyl-3(R),4(S)-dihydroxy-6-methylheptane.

Using the procedure of Example 21. but replacing TBA-CHA with [(1-Cbz-4-piperazinyl)carbonyl]-Phe, gave the desired compound.

EXAMPLE 124

[(1-Piperazinyl)carbonyl]-Phe-His Amide of 2(S)-Amino-1-cyclohexyl-3(R),4(S)-dihydroxy-6-methylheptane Bis-Acetic Acid Salt.

Using the procedure of Example 62 gave the desired compound in 90% yield. Mass spectrum: $(M+H)^+ = 640$ (free base).

EXAMPLE 125

[(4-Morpholinyl)carbonyl]-(4-OCH$_3$)Phe methyl ester.

Using the procedure of Example 116 but replacing H-Phe-OCH$_3$ HCl with L-tyrosine methyl ester methyl ether HCl gave the title compound.

EXAMPLE 126

[(4-Morpholinyl)carbonyl]-(4-OCH$_3$)Phe-OH. the procedure of Example 73 gave the title compound in 92% yield.

EXAMPLE 127

[(4-Morpholinyl)carbonyl]-(4-OCH3)Phe-His Amide of 2(S)-Amino-1-cyclohexyl-3(R),4(S)-dihydroxy-6-methyl-heptane Using the procedure of Example 21, but replacing TBA-CHA with [(4-morpholinyl)carbonyl]-(4-OCH3)Phe gave the desired compound. Mass spectrum: $(M+H)^+ = 671$.

EXAMPLE 128

[4-(2-Oxopiperazinyl)carbonyl]-Phe methyl ester.

Using the procedure of Example 116, but replacing morpholine with 2-oxopiperazine [Transition Met. Chem., 11, 27 (1986)]gave the desired compound in 80% yield.

EXAMPLE 129

[4-(2-Oxopiperazinyl)carbonyl]-Phe.

Having the procedure of Example 73 have the desired compound.

EXAMPLE 130

[4-(2-Oxopiperazinyl)carbonyl]-Phe-His Amide of 2(S)-Amino-1-cyclohexyl-3(R),4(S)-dihydroxy-6-methylheptane.

Having the procedure of Example 21, but replacing TBA-CHA with (4-(2- oxopiperazinyl)carbonyl]-Phe, gave the desired product in 60% yield.

EXAMPLE 131

[1-(4-Oxopiperidinyl)carbonyl]-Phe methyl ester.

Having the procedure of Example 116, but replacing morpholine with 4-oxopiperidine gave the desired compound.

EXAMPLE 132

[1-(4-Oxopiperidinyl)carbonyl]-Phe.

Using the procedure of Example 73 gave the desired compound in 91% yield.

EXAMPLE 133

[1-(4-Oxopiperidinyl)carbonyl]-Phe-His Amide of 2(S)-Amino-1-cyclohexyl-3(R),4(S)-dihydroxy-6-methylheptane.

Using the procedure of Example 21, but replacing TBA-CHA with [1-(4-oxopiperidinyl)carbonyl]-Phe, gave the desired product.

EXAMPLE 134

[1-(4-Hydroxypiperidinyl)carbonyl]-Phe methyl ester.

Using the procedure of Example 116, but replacing morpholine with 4-hydroxypiperidine, gave the desired compound.

EXAMPLE 135

[1-(4-Hydroxypiperidinyl)carbonyl]-Phe.

Using the procedure of Example 73, gave the desired product in 82% yield.

EXAMPLE 136

[1-(4-Hydroxypiperidinyl)carbonyl]-Phe-His Amide of 2(S)-Amino-1-cyclohexyl-3(R),4(S)-dihydroxy-6-methylheptane.

Using the procedure of Example 21, but replacing TBA-CHA with [1-(4-hydroxypiperidinyl)carbonyl]-Phe, gave the desired compound in 56% yield.

EXAMPLE 137

[1-(3-HydroxYpiperidinyl)carbonyl]-Phe-His Amide of 2(S)-Amino-1-cyclohexyl-3(R),4(S)-dihydroxy-6-methylheptane.

Using the procedures described in Examples 116, 73 and 21, the title compound was synthesized.

EXAMPLE 138

3-Carbomethoxy-3-phenoxypropionic acid.

A solution of 2-phenoxybutyrolactone [Dareman, C., Bull. Soc. Chim. Fr., 294 (1971), 4 96 g, 0.028 mol] was added to methanol (125 mL) containing 0.054 mol of sodium methoxide. After stirring for 3.5 hours at room temperature, the mixture was quenched with 5 mL of acetic acid, and then distributed between ether and brine solution. The organic layer was washed with brine and evaporated to a residue (methyl-4-hydroxy-2-phenoxybutyrate). A solution of this material in acetone (300 mL) was treated with Jones solution until the orange color persisted. The acetone was partially evaporated and the residue was distributed between ether and brine solution. Evaporation of the dried ether layer gave the desired product as a waxy solid. NMR (300 NMR, CDCl$_3$): 3.02 (d, 2H), 3.78 (s, 3H), 5.11 (t, 1h).

EXAMPLE 139

3-[(4-Morpholinyl)carbonyl]-2-phenoxypropionic acid methyl ester.

Using the mixed anhydride procedure described in Example 2, morpholine was coupled to 3-carbomethoxy-3-phenoxypropionic acid to give the desired product in 86% yield, mp 83°-84° C. Anal. Calcd for C$_{15}$H$_{19}$NO$_5$: C, 61.42; H, 6.53; N, 4.78. Found: C, 61.47; H, 6.50; N, 4.61.

EXAMPLE 140

3-[(4-Morpholinyl)carbonyl]-2-phenoxypropionic acid.

Using the procedure of Example 73 gave the desired product in 59% yield, mp 150°-151° C.

EXAMPLE 141

3-[(4-Morpholinyl)carbonyl]-2(R,S)-phenoxypropionyl-His Amide of 2(S)-Amino-1-cyclohexyl-3(R),4(S)-dihydroxy-6-methylheptane.

Using the procedure of Example 21, but replacing TBA-CHA with the resultant product of Example 140, gave the desired product as a mixture of R and S diastereomers. Chromatography on silica (dichloromethane/methanol, 95/5) provided the less polar diastereomer (isomer A) and the more polar diastereomer (isomer B). Isomer A: Mass spectrum: (M+H)+ =642. Analysis calculated for C$_{34}$H$_{51}$N$_5$O$_7$ ½ H$_2$O: C, 62.7; H, 8.0; N, 10.7. Found: C, 62.7; H, 8.1; N, 10.3. Isomer B: Mass spectrum: (M+H)+ =642. Analysis calculated for C$_{34}$H$_{51}$N$_5$O$_7$ H$_2$O: C, 61.9; H, 8.1; 10.6. Found: C, 62.2; H, 7.8; N, 10.4.

EXAMPLE 142

2(R,S)-(4-Morpholinylcarbonylmethyl)-3-phenylpropionic Acid.

Ethyl a-carboxymethylcinnamate was prepared as reported (Cohen, S. G. and Milovanovic, A. Biochemistry, 1968, 3495) and hydrogenated according to the procedure of Example 93. The resulting dihydrocinnamate was coupled to morpholine using the procedure of Example 21. Ester hydrolysis according to the procedure of Example 73 provided the desired compound. Mass spectrum: (M+H)+ =278. Anal. Calcd for C$_{15}$H$_{13}$NO$_4$ ¼ H$_2$O: C, 64.4; H, 6.9; N, 5.0. Found: C, 64.4; H, 6.8; N, 4.9.

EXAMPLE 143

2(R,S)-(4-Morpholinylcarbonylmethyl)-3-phenylpropionyl-His Amide of 2(S)-Amino-1-cyclohexyl-3(R),4(S)-dihydroxy-6-methylheptane.

Using the procedure of Example 21, but replacing TBA-CHA with 2(R,S)-(4-morpholinylcarbonylmethyl)-3-phenylpropionic acid provided the desired product as a mixture of R and S diastereomers. Chromatography on silica (dichloro- methane/methanol 95/5-90/1) provided the less polar diastereomer (isomer A) and the more polar diastereomer (isomer B). Isomer A: Mass spectrum: (M+H)+ =640. Anal. Calcd for C$_{35}$H$_{53}$N$_5$O$_6$ ½ H$_2$O: C, 64.8; H, 8.4; N, 10.8. Found: C, 65.1; H, 8.4, N, 10.3. Isomer B: Mass spectrum: (M+H)+ =640. Anal. Calcd for C$_{35}$H$_{53}$N$_5$O ½ H$_2$O: C, 64.8; H, 8.4; N, 10.8. Found: C, 65.0; H, 8.3; N, 10.6.

EXAMPLE 144

N-(Benzyloxyacetyl)morpholine.

Using the mixed anhydride procedure described in Example 2, morpholine was coupled to benzyloxyacetic acid to give the desired product in 90% yield.

EXAMPLE 145

Methyl 2-benzyl-S-benzyloxy-3-[(4-morpholinyl)carbonyl]propionate.

A −78° C. solution of N-(benzyloxyacetyl)morpholine (1 g, 8.5 mmol) in THF (25 mL) was treated with potassium bis(trimethylsilyl)amide (17 mL of a 0.5M solution). After stirring for 10 min at −78° C., a solution of methyl 2-bromo-3-phenylpropionate (8.5 mmol) in THF (5 mL) was added dropwise. Stirring at −78° C. for 30 min was followed by warming to 0° C. The reaction was then distributed between ether and brine solution. The organic layer was washed with brine and dried over MgSO$_4$. Evaporation and flash chromatography on silica gel gave the desired product in 63% yield.

EXAMPLE 146

2-Benzyl-3-hydroxy-3-[(4-morpholinyl)carbonyl]-propionic acid.

Using the procedure of Example 84, the benzyl ether protecting group was removed by catalytic hydrogenolysis to give methyl 2-benzyl-3-hydroxy-3-[(4-morpholinyl) carbonyl]propionate. The methyl ester function was hydrolyzed using the procedure in Example 73 to give the title compound.

EXAMPLE 147

2-Benzyl-3-hydroxy-3-[(4-morpholinyl)carbonyl]propionyl -His Amide of 2(S)-Amino-l-cyclohexyl-3(R),4(S) dihydroxy-6-methylheptane.

Using the procedure of Example 21, but replacing TBA-CHA with 2-benzyl-3-hydroxy-3-[(4-morpholinyl)carbonyl] propionic acid, gave the desired product in 51% yield

EXAMPLE 148

2-Hydroxy-3-[(4-morpholinyl]carbonyl]propionic acid acetonide.

A mixture of dl-malic acid (5 g), 2,2-dimethoxypropane (100 mL) and catalytic p-TsOH was heated at 100° C. for 5 h. After cooling and evaporation the residual solid was recrystallized from carbon tetrachloride to give the corresponding acetonide lactone. This material was coupled to morpholine using the mixed anhydride procedure of Example 2 to give the title compound.

EXAMPLE 149

Methyl 2-hydroxy-3-[(4-morpholinyl)carbonyl]propionate.

A solution of 2-hydroxy-3-[4-(morpholinyl)-carbonyl]propionic acid acetonide (5 g) in methyl alcohol (75 mL) was treated with 1 mL of concentrated sulphuric acid and the mixture was stirred for 24 h at room temperature. Partial evaporation of the solvent gave a residue which
-70was distributed between either and brine solution. The ether layer was dried over MgSO$_4$ and evaporated to give the desired product.

EXAMPLE 150

Methyl 2-anilino-3-[(4-morpholinyl)carbonyl]propionate. The trifluoromethanesulfonate of methyl 2-hydroxy-3-[4-morpholinyl)carbonyl]propionate was prepared by the method of Shiosaki [J. Org. Chem., 46, 3230 (1981)]. A solution of this compound (7 mmol) in methylene chloride (25 mL) was added dropwise within 5 minutes at room temperature to a stirred solution of aniline (14 mmol) in methylene chloride (25 mL), and stirring continued for 30 min at room temperature. The reaction mixture was filtered, the solution was washed with water, dried over Na$_2$SO$_4$, concentrated and the residue purified by chromatography. Yield of product=80%.

EXAMPLE 151

2-Anilino-3-[(4-morpholinyl)carbonyl]propionyl-His Amide 2(S)-Amino-l-cyclohexyl-3(R),4(S)-dihydroxy-6-methylheptane.

Using the product from Example 150 and the methods of Examples 73 and 21 gave the title compound.

EXAMPLE 152

Ethyl 5-Acetamido-2(R,S)-benzyl-4-oxopentanoate.
Ethyl a-carboxymethylcinnamate was prepared as reported (Cohen, S. G. and Milovanovic, A. Biochemistry, 1968, 495) and hydrogenated according to the procedure of Example 93. The resulting acid was converted to the desired acetamidomethyl ketone using the methodology of Pfaltz et al., (Tetrahedron Lett. 1984, 25, 2977: acid to acid chloride to cyanoketone followed by Zn/acetic acid/acetic anhydride treatment).

EXAMPLE 153

5-Acetamido-2(R,S)-benzyl-4-oxopentanoyl-His Amide of 2(S)-Amino-l-cyclohexyl-3(R).4(S)-dihYdroxY-6-methylheptane.

The resultant product of Example 152 was hydrolyzed according to the procedure of Example 73 provided the corresponding acid which was coupled in place of TBA-CHA according to the procedure of Example 21. The desired product was obtained as an (R,S) mixture which was separated by chromatography.

EXAMPLE 154

3-[(4-Morpholinyl)carbonyl]-2-thiophenoxypropionic acid methyl ester.

Using the procedure of Example 139, but replacing 3-carbomethoxy-3-phenoxypropionic acid with 3-carbomethoxy-3-thiophenoxypropionic acid, gave the desired product.

EXAMPLE 155

3-[(4-Morpholinyl)carbonyl]-2-(R,S)-thiophenoxypropionyl-His Amide of 2(S)-Amino-l-cyclohexyl-3(R),4(S)-dihydroxy-6-methylheptane.

Using the procedures of Examples 73 and 21, the title compound was prepared in 49% overall yield.

EXAMPLE 156

2(S)-t-Butyloxycarbonylamino-l-cyclohexyl-3-hydroxy-6-methylheptan-4-one.

To a solution of resultant compound of Example 13 (8.50, 27.5 mmol) in dry THF (150 mL) were added OsO$_4$ (2.8 mL of a 2.5% solution in t-butanol and N-methylmorpholine N-oxide (9.28 g, 68.7 mmol). After 4d the mixture was partitioned between either (200 mL) and brine (100 mL). The aqueous layer was back-extracted with either (2×100mL), and the combined organic phase was washed with 10% Na$_2$SO$_3$, 0.1 M H$_3$PO$_4$, and brine. Drying (MgSO$_4$) and evaporating provided a residue (10.81 g) which was chromatographed on silica gel to remove the four diastereomeric diols from 0.70 g (7%) of the desired product. Mass spectrum: (M+H)=342.

EXAMPLE 157

Boc-Phe-His Amide of 2(S)-t-Butyloxycarbonylamino-l-cyclohexyl-3-hydroxy-6-methylheptan-4-one.

The resultant product of Example 156 (220 mg, 0.645 mmol) was treated with 4 M HCl/dioxane for 6 hours. Evaporation and drying under high vacuum provided the corresponding amine hydrochloride which was dissolved in dry dimethylformamide (DMF, 1.0 mL), treated with Boc-Phe-His (260 mg), N-methylmorpholine (0.142 mL), and 1-hydroxybenzotriazole hydrate (261 mg), cooled to 23° C., and then treated with 1-ethyl-3-(dimethylaminopropyl) carbodiimide Hydrochloride (124 mg). Evaporation after 16 h provided a thick oil which was partitioned between ethylacetate (60 mL) and saturated NaHCO$_3$ (30 mL). The organic phase was washed with brine, dried (MgSO$_4$), and evaporated to give a residue which was chromatographed on silica gel (dichloromethane/methanol) to give 161 mg (40%) of the desired product. Mass spectrum: (M+H)$^+$ =626. Anal. calcd. for C$_{34}$H$_{51}$N$_5$O$_6$: % C, 65.3; H, 8.3; N, 11.2. Found: % C, 65.6; H, 8.3; N, 11.2.

EXAMPLE 158

Boc-Phe-His Amide (at N-2) of 1-Cyclohexyl-2(S),4-(R,S)-diamino-3-hydroxy-6-methylheptane.

Treatment of the resultant compound of Example 157 with hydroxylamine followed by reduction of the oxime over platinum oxide gave the desired product.

EXAMPLE 159

Ethoxycarbonyl-Phe-Leu Amide of 1-Cyclohexyl-2(S), 3(R,S) -diamino-4-hydroxy-6-methylheptane.

The resultant compound of Example 36 was acetylated acetic anhydride and the corresponding 3-hydroxy-4-acetoxy compound was isolated by silica gel chromatography. Oxidation to the 3-one using Jones reagent, deacetylization using sodium methoxide in methanol, and reductive amination as in Example 158 gave the desired product.

EXAMPLE 160

Ethoxycarbonyl-Phe-His Amide of 2(S)-Amino-1-phenyl-3(R), 4(S)-dihydroxy-6-methylheptane.

Using the procedure of Example 13, but replacing Boc-cyclohexylalanine methyl ester with Boc-Phe-OCH$_3$ and then following the procedures of Examples 14 and 29 gave the desired product.

EXAMPLE 161

Cyclic Carbonate of 2(S)-t-Butyloxycarbonylamino-1-cyclohexyl-3(R),4(S)-dihydroxy-6-methylheptane.

The 3(R),4(S)diastereomer of Example 14 was heated with N,N'-carbonyldiimidazole in benzene to give the desired compound in 86% yield.

EXAMPLE 162

D-Ser-Phe-His amide of 2(S)-Amino-1-cYclohexYl-3(R),4(S)-dihydroxy-6-methylheptane.

Following the procedure of Example 15, but replacing the resultant product of Example 14 with the resultant product of Example 161 and replacing Boc-Phe-His with Cbz-D-Ser-Phe-His gave the desired N,O-diprotected material. N-deprotection following the procedure of Example 62 followed by O-deprotection with 0.5M NaOH in 50% aq. dioxane, gave the desired compound.

EXAMPLE 163

2(S)-Isobutyrylmercapto-3-phenylpropionyl-Phe-His Amide of 2(S)-Amino-1-cyclohexyl-3(R),4(S)-dihydroxy-6-methylheptane.

S(+)-2-mercapto-3-phenylpropionic acid was prepared as described (Acton, N and Komoriya, A. *Organic Preparation and Procedures Int.* 1982, 14, 381–392.) and acylated with isobutyric anhydride. Replacing TBA-CHA with this acid and using the procedure of Example 21, gave the titled compound.

EXAMPLE 164

2(S)-[(2-Aminoethyl)mercapto]-3-phenypropionyl-Phe-His Amide of 2(S)-Amino-1-cyclohexyl-3(R),4(S)-dihydroxy-6-methylheptane.

2(S)-[(2-Aminoethyl)mercapto]-3-phenylpropionic acid was made using literature methodology (Acton, N. and Komoriya, A. *Organic Preparations and Procedures Int.* 1982, 14, 381–392.) Replacing TBA-CHA with this acid and using the procedure of Example 21, gave the titled compound.

EXAMPLE 165

(2S,3R,5R)-2-(t-Butyloxycarbonylamino)-3-hydroxy-7-methyl-1-phenyloctane-5-carboxylic Acid Lithium Salt A solution of 27.1 mg (0 075 mmol) of (3R, 5R, 1S)-5-[(t-butyloxycarbonylamino)-2-phenylethyl]-3-isobutyl-dihydrofuran-2-(3H-)-one (D. J. Kempf, *J. Org. Chem.* 1986, 51, 3921) in 1 mL of dioxane was treated with 185 μl (0.092 mmol) of LiOH (0.5 M in H$_2$O) and stirred at ambient temperature for 8 h. Removal of the solvent in vacuo gave the desired compound as a white solid.

EXAMPLE 166

(2S,3R,5R)-3-(t-Butyldimethylsilyloxy)-2-(t-butyloxycarbonylamino)-7-methyl-1-phenyloctane-5-carboxylic Acid t-Butyldimethylsilyl Ester A solution of the resultant compound of Example 165 (0.075 mmol), 42 mg (0.28 mmol) of t-butyldimethylsilyl chloride and 31 mg (0.45 mmol) of imidazole in 0.8 mL of dimethylformamide was allowed to stand at ambient temperature for 2 days. Removal of the solvent in vacuo gave the crude desired compound.

EXAMPLE 167

(2S,3R,5R)-3-(t-Butyldimethylsilyloxy)-2-(t-butyloxycarbonylamino)-7-methyl-1-phenyloctane-5-carboxylic Acid Lithium Salt A solution of the crude resultant compound of Example 166 (0.075 mmol) in 2 mL of dioxane was treated with 0.6 mL (0.3 mmol) of LiOH (0.5 M in H$_2$O) and allowed to stir at ambient temperature for 2 days. After removal of the solvent, purification by flash column chromatography using 3% methanol/chloroform gave 18.3 mg (49%) of the desired compound (R$_f$ 0.10, 2% methanol/chloroform).

EXAMPLE 168

3-(t-butyldimethylsilyloxy)-2-(t-butyloxycarbonyl amino)-8-(cyclohexylmethyl)-9,10-dihydroxy-5-isobutyl-12-methyl-l-phenyltridecane Using the coupling procedure of Example 21 but replacing Boc-Phe-His-OH with the resultant compound of Example 167 gave the desired compound in 62% yield after purification by MPLC using 6:1 hexane/ethyl acetate (R$_f$0.50, 2:1 hexane/ethyl acetate).

EXAMPLE 169

(2S, 3R, 5R, 8S, 9R, 10S)-7-Aza-2-(t-butyloxycarbonylamino)-8-(cyclohexylmethyl)-5-isobutyl-l2-methyl-l-phenyl-3,9,10-trihydroxytridecane A solution of 16.5 mg (0.023 mmol) of the resultant compound of Example 168 in 1 mL of tetrahydrofuran was treated with 70 mL (0.07 mmol) of tetra-n-butylammmonium fluoride (1 M in tetrahydrofuran) and allowed to stir at ambient temperature for 16 h. After concentration in vacuo, separation by MPLC using 2:1 hexane/ethyl acetate gave 10.5 mg (76%) of the desired compound as a white crystalline solid. Mass spectrum: $(M+H)^+ = 605$.

EXAMPLE 170

Cbz-6-aminohexanoyl-(4-methoxy)phenylalanine Benzyl Ester

Using the procedure of Example 72 but replacing 3-benzyloxycarbonylamino-3-methylbutanoic acid with 6-(Cbz-amino)-n-caproic acid and replacing phenylalanine methyl ester with (4-methoxy)phenylalanine benzyl ester gave, after purification by flash column chromatography using 9:1 chloroform/ethyl acetate, a 38% yield of the desired compound.

EXAMPLE 171

Cbz-6-aminohexanoyl-(4-methoxy)phenylalanine

A solution of 2.66 g (5 mmol) of the resultant compound of Example 170 in 60 mL of tetrahydrofuran was cooled to 0° C, treated with 0.63 g (15 mmol) of LiOH in 30 mL of H$_2$O and allowed to stir for 2 h. After concentration of the solvent, the mixture was partitioned between H$_2$O and ether, acidified, extracted with ethyl acetate, dried over MgSO$_4$ and concentrated to give 1.55 g (70%) of the desired compound.

EXAMPLE 172

Cbz-6-aminohexanoyl-(4-methoxy)Phe-His Amide of (2S,3R,4S)-2-Amino-1-cyclohexyl-3,4-dihydroxy-6-methylheptane.

Using the procedure of Example 21 but replacing TBA-CHA with the resultant compound of Example 171 gave, after recrystallization from ethyl acetate, a 79% yield of the desired compound. Mass spectrum: $(M+H)^+ = 805$.

EXAMPLE 173

6-Aminohexanoyl-(4-methoxy)Phe-His Amide of (2S, 3R, 4S)-2-Amino-1-cyclohexyl-3,4-dihydroxy-6-methylheptane Diacetate Salt.

A mixture of 0.97 g (1.2 mmol) of the resultant compound of Example 172 and 0.20 g of 20% palladium on carbon in 150 mL of 95% aqueous acetic acid was shaken in a Parr Apparatus under four atmospheres of H$_2$. After filtration to remove catalyst, the solution was concentrated in vacuo, diluted with 75 mL of H$_2$O, and concentrated by lyophilization to give 0.86 g (91%) of the desired compound as a white solid. Mass spectrum: $(M+H)^+ = 671$.

EXAMPLE 174

[(4-Morpholinyl)carbonyl-D-Phe-His Amide of 2(S)-Amino-1-cyclohexyl-3(R),4(S)-dihydroxy-6-methylheptane.

Using the procedures of Examples 116, 117 and 118 but replacing L-Phe-OCH$_3$ HCl with D-Phe-OCH$_3$ HCl, gave the title compound. Mass spectrum: $(M+H)^+ = 641$.

EXAMPLE 175

Ethyl Hydrogen (alpha,alpha-dimethylbenzyl)malonate.

Diethyl (alpha,alpha-dimethylbenzyl)malonate was prepared by the congugate addition of phenyl magnesium bromide to diethyl isopropylidenemalonate as described by C. Holmberg [*Liebigs Ann. Chem.*, 748 (1981)]. A solution of this diester (42.1 g, 0.15 mole) in ethanol (100 mL) was treated by dropwise addition with a solution of potassium hydroxide (8.48 g, 0.13 mole) in 100 mL of ethanol. After heating at 90° C. for 1 h and at 50° C. for 20 h, the reaction mixture was evaporated on the rotary evaporator to a residue. The residue was diluted with water and extracted with ether to remove unreacted starting material. The aqueous phase was cooled to 5° C., acidified to pH 3, with 6N HCl and extracted with methylene chloride. The organic layer was washed with brine solution and dried over magnesium sulfate. Evaporation of the solvent gave 27.3 g (84%) of liquid product. NMR (CDCl$_3$) 1.05 (3H, t), 1.6 (6H, s), 3.78 (1H, s), 3.96 (2H, m), 7.2–7.4 (5H, m).

EXAMPLE 176

Ethyl 2(R,S)-[[(4-morpholinyl)carbonyl]amino]-3,3-dimethyl-3-phenylpropionate.

To a solution of ethyl hydrogen ( -dimethylbenzyl) malonate (4 g, 0.016 mole) in toluene was added triethylamine (2.23 mL, 0.016 mole) and diphenylphosphoryl azide (4.4 g, 0.016 mole). The reaction mixture was heated at 100° C. for 2.5 h, cooled to 5° C., and treated with 1.4 mL (0.016 mole) of morpholine. After stirring overnight at room temperature, the toluene solution was washed successively with 1N HCl and aqueous sodium bicarbonate solution. The dried organic solution was evaporated to a residue which was purified by column chromatography on silica gel. There was obtained 3.7 g (69%) of product after trituration with hexane, mp 93°–94° C.

Anal. calcd. for C$_{18}$H$_{26}$N$_2$O$_4$: C, 64.65; H, 7.84; N, 8.38.

Found: C, 64.72; H, 7.95; N, 8.33.

EXAMPLE 177

2(R,S)-[[(4-Morpholinyl)carbonyl]amino]-3,3-dimethyl-3-phenylpropionic Acid.

A solution of the product form Example 176 (2 g, 5.99 mmole) in dioxane (10 mL) was treated with 0.26 g (6.5 mmol) of sodium hydroxide in 5 mL of water. After

EXAMPLE 178

2(R,S)-[[(4-Morpholinyl)carbonyl]amino]-3,3-dimethyl-3-phenylpropionyl-His Amide of 2(S)-Amino-1-cyclohexyl-3(R),4(S)-dihydroxy-6-methylheptane.

The product from Example 20 was deprotected with HCl/methanol and coupled to the product from Example 177 using the procedure described in Example 5 but modified as follows. HOBT was not used in the coupling and the reaction time was 20 h. There was obtained an 80% yield of the desired product. Mass spectrum: $(M+H)^+ = 669$.

EXAMPLE 179

H-Isonipecotyl-(4-OCH$_3$)Phe-His Amide of 2(S)-Amino-1-cyclohexyl-3(R),4(S)-dihydroxy-6-methylheptane Diacetic Acid Salt.

Using the procedure of Examples 67 and 68, but replacing Cbz-isonipecotyl-Phe with Cbz-isonipecotyl-(4-OCH$_3$)-Phe gave the desired product. Mass spectrum: $(M+H)^+ = 669$ (free base).

EXAMPLE 180

H-[(β,β-di-Me)-β-Ala]-(4-OCH$_3$)Phe-His Amide of 2(S)-Amino-1-cyclohexyl-3(R),4(S)-dihydroxy-6-methylheptane Diacetic Acid Salt.

Using the procedures of Examples 74 and 75, but replacing Cbz-[(8,B-di-Me)-B-Ala]-Phe with Cbz-8(β,β-di-Me)-β-Ala]-(OCH$_3$)Phe gave the desired product. $(M+H)^+ = 657$ (free base).

EXAMPLE 181

2(S)-t-Butyloxycarbonylamino-1-cyclohexyl-3(R)-hydroxy-6-methylheptan-4-one

To a stirred −63° C. solution of oxalyl chloride (784 mg, 6.18 mmol) in dry dichloromethane (15 mL) was added dry dimethylsulfoxide (708 mg, 9.06 mmol) dropwise over 5 minutes. After another 5 minutes, Boc-cyclohexylalaninol (1.06 g, 4.12 mmol) in dichloromethane (5 mL) was added dropwise over 5 minutes, and 5 minutes later, triethylamine (1.67 g, 16.48 mmol) was added similarly. ZnI$_2$ (300 mg, 0.94 mmol) was added over 5 minutes. After stirring for 2 minutes, trimethylsilyl cyanide (1.43g, 14.42 mmol) was added and the mixture was warmed to room temperature for 1 hour. The mixture was then cooled to 0° C. and isobutylmagnesium chloride (22.0 mL of a 2 M soln. in ether) was added. After warming to room temperature for 4 hours, the mixture was poured into 1 M H$_3$PO$_4$ (40 mL)/ice (50 mL) and extracted with ethyl acetate. The combined organic phase was washed sequentially with 1 M H$_3$PO$_4$, water, satd. NaHCO$_3$, and brine. Drying (MgSO$_4$), filtering, and evaporating provided 1.75 g of an oil which was dissolved in THF (75 mL) and treated with 1 M H$_3$PO$_4$ (25 mL) for 18 hours at 5° C. The solution was partitioned between ethyl acetate/brine, and the resulting organic phase was washed sequentially with brine, satd. NaHCO3, and brine. Drying (MgSO$_4$), filtering, and evaporating provided the desired product (1.39 g, 99%) which was used directly in the next step.

stirring for 16 h at 35° C., the reaction was worked up as described in Example 175 to give a 93% yield of product.

EXAMPLE 182

2(S)-t-Butyloxycarbonylamino-1-cyclohexyl-3(R),4(S)-dihydroxy-6-methylheptane

To a stirred solution of 2(S)-t-Butyloxycarbonylamino-1-cyclohexyl-3(R)-hydroxy-6-methylheptan-4-one (200 mg, 0.586 mmol) in THF (10 mL) was added NaBH$_4$ (22 mg, 0.586 mmol). After 2 hours, the solvent was evaporated and the residue was partitioned between ethyl acetate and brine. The organic phase was washed (brine), dried (MgSO$_4$), filtered and evaporated. The residue was recrystallized from methylcyclohexane to give 76 mg (38%) of the desired product. M.p. 130°–131° C. The mother liquor was chromatographed (silica gel, ether/hexane) to afford 43 mg (21%) more.

EXAMPLE 183

(2S,3R,5R,8S,9R,10S)-7-Aza-2-(t-Butyloxycarbonylamino)-8-(cyclohexylmethyl)-12-methyl-5-(4-pentenyl)-1-phenyl-3,9,10-trihydroxytridecane Using the procedures of Examples 165-169, but replacing (3R,5R,1S)-5-[(t-butyloxycarbonylamino)-2-phenylethyl]-3-isobutyldihydrofuran-2-(3H)-one- with (3R,5R,1S)-5-[-(t--butyloxycarbonylamino)-2-phenylethyl]-3-(4-pentenyl)dihydrofuran-2-(3H)-one (D. J. Kempf, *J. Org. Chem.* 1986, 51, 3921) gave the desired compound in 52% yield after purification by MPLC using 2:1 hexane/ethyl acetate. Mass spectrum: $(M+H)^+ = 617$.

EXAMPLE 184

4-Carboxybutyroyl-Phe-Leu Amide of 2(S)-Amino-1-cyclohexyl-3(R),4(S)-dihydroxy-6-methylheptane To the resultant compound of Example 57 (0.5 g, 0.99 mmol) dissoved in dimethylformamide (10 ml), was added glutaric anhydride (0.11 g, 0.99 mmol). After stirring the reaction mixture for 24 h at room temperature, the solvent was evaporated and the resulting residue was partitioned between ethyl acetate and water. The organic phase was washed (brine) and dried (Na$_2$SO$_4$). Filtering and evaporation provided crude material which was chromatographed (CH$_3$OH:CH$_2$Cl$_2$, 5:95–10:90) to give 0.39 g of the desired compound, m.p. 195°–198° C. Mass spectrum: $(M+H)^+ = 618$. Anal. Calcd. for C$_{34}$H$_{55}$N$_3$O$_7$H$_2$O: C, 64.23; H, 9.04; N, 6.61. Found: C, 64.36; H, 8.76; N, 6.56.

EXAMPLE 185A

[1(S)-(Ethoxycarbonyl)-ethyl]-Phe-benzyl ester

A mixture of ethyl pyruvate (4.17 g, 36 mmol), phe-benzyl ester p-toluenesulfonic acid salt (14.4 g, 34 mmol) and NaOAc (5.53 g, 67 mmol) in 200 ml of absolute ethanol was stirred at 0° C. for 30 min. NaCNBH$_3$ (2.19 g, 34.7 mmol) in 200 ml of absolute ethanol was added dropwise over one hour. After the addition was complete, the reaction mixture was stirred at room temperature for 36 h. The mixture was filtered and the filtrate was evaporated under reduced pressure. The resulting oil was chromatographed, eluting with ethyl acetate/hexane (1:4), to afford 3.5 g of less polar diastereomer and 1.5 g of more polar diastereomer (the desired product). Mass spectrum (more polar isomer): $(M+H)^+ = 365$. NMR (CDCl$_3$): 0.9 (6H, q), 1.1 (3H, t), 1.2 (3H, d), 1.4–1.7 (11H, m), 4.1 (2H, m), 6.8 (1H, s), 7.3 (5H, m), 7.5 (1H, s).

EXAMPLE 185B

[l(S)-(Ethoxycarbonyl)-ethyl]-Phe-His Amide of 2(S)-Amino-l-cyclohexyl-3(R),4(S)-dihydroxy-6-methylheptane The more polar diastereomer isolated in Example 185 (700 mg, 1.97 mmol) was hydrogenated with 10% Pd/C at 4 atmospheres of $H_2$ in ethanol for several hours. The mixture was filtered and the filtrate was evaporated under reduced pressure. The resultant crude product of the reduction (130 mg, 0.49 mmol) was coupled to the His-Amide of 2(S)-Amino-l-cyclohexyl-3(R),4(S)-dihydroxy-6-methylheptane dihyrochloride (190 mg, 0.42 mmol), following the procedure of Example 5. The product was chromatographed, eluting with 5% methanol/chloroform, to afford 120 mg of the desired product, m.p. 84°–86° C. Mass spectrum: (M+H)+ =628. NMR (CDCl3); 0.9 (6H, q), 1.1 (3H, t), 1.2 (3H, d), 1.4–1.7 (11H, m), 4.1 (2H, m), 6.8 (1H, s), 7 3 (5H, m), 7.5 (1H, s).

EXAMPLE 186

Carboxymethoxymethylcarbonyl-Phe-His Amide of 2(S)-Amino-l-cyclohexyl-3(R),4(S)-dihydroxy-6-methylheptane A mixture of diglycolic anhydride (66 mg, 0.568 mmol) and Phe-His amide of 2(S)-amino-l-cyclohexyl-3(R),4(S)-dihydroxy-6-methylheptane (300 mg, 0.569 mmol) in 7 ml of DMF was stirred at room temperature for 16 h. The DMF was evaporated at reduced pressure. The resulting residue was treated with ethyl acetate to obtain a precipitate. The crude product was purified from methanol/ethyl acetate to afford 230 mg of the desired product. Mass spectrum: (M+H)+ =644. NMR (DMSO): 0.8 (6H, q), 1–1.3 (11H, m), 3.9 (2H, s), 4 (2H, s), 6.9 (1H, s), 7 (1H, s).

EXAMPLE 187

3-Benzyloxycarbonyl-4-(4-carboxybutyl)oxazolidin-5-one

A solution of 3.0 g (17.1 mmol) of dl-alpha-aminopimelic acid in 30 ml of dioxane and 10 ml of water was treated simultaneously in a dropwise fashion with 4.8 g (18.8 mmol) of N-(benzyloxycarbonyloxy)succinimide in 10 ml of dioxane and 17 ml (51 mmol) of 3 N NaOH. After the addition was complete, the reaction mixture was stirred for 1.5 h and concentrated in vacuo. The residue was taken up in dilute NaOH, washed with chloroform, acidified to pH 1 with concentrated HCl, extracted with three 200 ml portions of chloroform, washed with saturated brine, dried over $MgSO_4$, and concentrated to give 3.21 g of a white solid. The solid was taken up in benzene along with 0.17 g (0.57 mmol) of p-toluenesulfonic acid monohydrate and 0.57 g of paraformaldehyde. The resulting suspension was heated at reflux with azeotropic removal of water for 7 h. The solution was washed with two 10 ml portions of water and extracted with 100 ml of 1 M $NaHCO_3$. The basic layer was cooled to 0° C., acidified with concentrated HCl, extracted with three 200 ml portions of ethyl acetate, dried over $MgSO_4$, and concentrated. Purification by silica gel chromatography using 10% methanol in chloroform as eluent gave 2.61 g of the desired compound. Mass spectrum: M+ =321.

EXAMPLE 188

N-[5[3-(Benzyloxycarbonyl)oxazolidin-5-on-4-yl]pentanoyl]-(4-OMe)-Phe-Leu Amide of 2(S)-Amino-l-cyclohexyl-3(R).4(S)-dihydroxy-6-methylheptane The resultant compound of Example 187 was coupled to the resultant compound of Example 55 using the procedure of Example 57. Silica gel chromatography using 5% methanol in chloroform as eluent provided the desired compound, m.p. 133° C. Mass spectrum: (M+H)+ =837. NMR (CDCl3): 0.90 (d, J=7Hz, 3H), 0.92 (d, 7Hz, 6H), 0.96 (d, J=7Hz, 3H), 1.1–2.0 (br envelope, 2.16 (br t, 2H), 3.02 (m, 2H), 3.20 (m, 2H), 3.29 (m, 1H), 3.80 (s, 3H), 4.16 (m, 1H), 4.30 (m, 2H), 4.42 (m, 1H), 5.20 (AA', 2H), 5.52 (br, 1H), 5.92 (br, 1H), 6.13 (br, 1H), 6.47 (br d, 1H), 6.86 (d, J=9Hz, 2H), 7.12 (d, J=9Hz, 2H), 7.37 (m, 5H).

EXAMPLE 189

6-Carboxy-6-(dimethylamino)hexanoyl-(4-OMe)-Phe-Leu Amide of 2(S)-Amino-l-cYclohexYl-3(R),4(S)-dihydroxy-6-methylheptane A mixture of 50 mg of the resultant compound of Example 188, 16 mg of 10% palladium on carbon, 0.45 ml of 37% aqueous formaldehyde and 5.5 mg of sodium acetate in 5 ml of methanol was stirred under a hydrogen atmosphere for 12 h. The resulting mixture was filtered through Celite, diluted with chloroform, dried over $Na_2SO_4$ and concentrated. The crude product was purified by silica gel chromatography using 10–20% methanol in chloroform as eluent to give the desired compound as a white solid. m.p. 155°–157° C. Mass spectrum: (M+H)+ =719. NMR (d6-DMSO): 0.79 (d, J=7Hz. 3H). 0.87 (m. 9H). 1.1–1.8 (br envelope), 2.02 (t, J=7Hz, 2H), 2.40 (br s, 6H), 2.65 (m, 1H), 2.95 (m, 3H), 3.07 (m, 1H), 3.71 (s, 3H), 4.13 (m, 1H), 4.33 (m, 1H), 4.42 (m, 1H), 6.81 (d, J=9Hz, 2H), 7.15 (d, J=9Hz, 2H), 7.63 (br, 1H), 8.00 (br d, J=8Hz, 1H), 8.19 (br, 1H).

EXAMPLE 190

6-(Benzyloxycarbonyl)amino-6-carboxyhexanoyl-(4-OMe)Phe-Leu Amide of 2(S)-Amino-l-cyclohexyl-3(R),4(S)-dihydroxy-6-methylheptane A solution of 35 mg (0.042 mmol) of the resultant compound of Example 188 in 2 ml of tetrahydrofuran and 1 ml of water was treated with 1.9 mg (0.046 mmol) of lithium hydroxide monohydrate. After completion of the reaction, the solution was acidified with HCl, extracted with chloroform, dried over $MgSO_4$, and concentrated to give the desired compound as a white solid, m.p. 93°–95° C. Mass spectrum: (M+H)+ =825. NMR (d6-DMSO): 0.79 (d, J=7Hz, 3H), 0.87 (m, 9H), 1.1–1.8 (br envelope), 1.99 (m, 2H), 2.64 (m. 1H), 2.93 (m, 3H), 3.05 (m, 1H), 3.69 (br s, 3H), 4.1–4.5 (m, 3H), 4 65 (m, 1H), 4.78 (m, 1H), 5.10 (m, 1H), 6.79 (br d, 2H), 7.13 (d, J=9Hz, 2H), 7.35 (m, 5H), 7.52 (br d, 1H), 7.96 (br d, 1H), 8.10 (br d, 1H).

EXAMPLE 191

6-(Benzyloxycarbonyl)amino-6-methoxycarbonyl Hexanoic Acid

A solution of 0.20 g (0.62 mmol) of the resultant compound of Example 187 in methanol was treated with sodium methoxide and stirred at ambient temperature for 2 h. The solvent was removed in vacuo, and the residue was acidified with 1N HCl, extracted with chloroform, and concentrated to give 159 mg of the desired compound.

EXAMPLE 192

6-(BenzYloxYcarbonyl)amino-6-(methoxycarbonyl)-hexanoyl-(4-OMe)Phe-Leu Amide of 2(S)-Amino-1-cyclohexyl-3(R),4(S)-dihydroxy-6-methylheptane The resultant compound of Example 191 was coupled to the resultant compound of Example 55 using the procedure of Example 157 to give the desired product, m p. 89° C. Mass spectrum: $(M+H)^+ = 839$. NMR $(CDCl_3)$ 0.90 (d, J=7Hz, 3H), 0.92 (d, J=7Hz, 6H), 0.96 (d, J=7Hz, 3H), 1.1-2.0 (br envelope), 2.16 (br t, J=7Hz, 2H), 3.02 (m, 2H), 3.20 (m, 1H), 3.28 (m, 1H), 3.74 (s, 3H), 3.79 (s, 3H), 4.17 (br, 1H), 4.32 (m, 2H), 4.41 (m, 1H), 5.11 (s, 2H), 5.41 (br t, J=9Hz, 1H), 6.01 (br, 1H), 6.15 (br, 1H), 6.46 (br d, 1H), 6.86 (d, J=9Hz, 2H), 7.35 (m, 5H).

EXAMPLE 193

6-Amino-6-(methoxycarbonyl)hexanoyl-(4-OMe)Phe-Leu Amide of 2(S)-Amino-1-cyclohexyl-3(R),4(S)-dihydroxy-6-methylheptane The resultant compound of Example 192 was hydrogenated using 10% palladium on carbon in methanol under 1 atmosphere of hydrogen to provide the desired compound, m.p. 178° C. Mass spectrum: $(M+H)^+ = 705$. NMR $(CDCl_3)$ 0.91 (m, 9H), 0.96 (d, J=7Hz, 3H), 1.1-2.0 (br envelope), 2.20 (t, J=7Hz, 2H), 3.04 (m, 2H), 3.20 (m, 1H), 3.29 (m, 1H), 3.39 (dd, J=8,5Hz, 1H), 3.72 (s, 3H), 3.81 (s, 3H), 4.34 (m, 2H), 4.45 (m, 1H), 6.12 (d, J=9Hz, 1H).

EXAMPLE 194

6-Amino-6-carboxyhexanoyl-(4-OMe)Phe-Leu Amide of 2(S)-Amino-1-cyclohexyl-3(R),4(S)-dihydroxy-6-methylheptane Using the prodecure of Example 190 with the resultant compound of Example 193 gave a crude lithium salt which was neutralized to pH 7 and extracted with chloroform to give the desired compound, m.p. 191°-192° C. Mass spectrum: $(M+H)^+ = 691$. NMR $(d_6\text{-DMSO})$: 0.59 (d, J=7Hz, 3H), 0.87 (m, 9H), 1.1-1.8 (br envelope), 2.01 (t, J=7Hz, 2H), 2.65 (m, 1H), 2.9-3.2 (m, 4H), 3.71 (s, 3H), 4.12 (m, 1H), 4.33 (m, 1H), 4.42 (m, 1H), 4.80 (m, 1H), 6.81 (d, J=9Hz, 2H), 7.15 (d, J=9Hz, 2H), 7.59 (br d, 1H), 8.00 (br d, 1H), 8.13 (br, 1H).

EXAMPLE 195

(4-OMe)Phe-His Amide of 2(S)-Amino-1-cyclohexyl-3(R),4(S)-dihydroxy-6-methylheptane Using the procedures of Example 83 and 84 but replacing Cbz-Phe-OH with Cbz-(4-OMe)Phe-OH gave the desired product.

EXAMPLE 196

N-5-[3-(Benzyloxycarbonyl)oxazolidin-5-on-4-yl]pentanoyl-(4-OMe)Phe-His Amide of 2(S) Amino-1-cyclohexyl-3(R),4(S)-dihydroxy-6-methylheptane Using the procedure of Example 188 but replacing the resultant compound of Example 55 with the resultant compound of Example 195 gave the desired compound, m.p. 144-146° C. (dec). Mass spectrum: $(M+H)^+ = 861$. NMR $(CDCl_3)$: 0.7-2.0 (br envelope), 0.92 (d, J=7Hz, 3H), 0.95 (d, J=7Hz, 3H), 2.18 (m, 2H), 2.91 (m,1H), 3.1-3.4 (m, 4H), 3.70 (m, 1H), 3.80 (s, 3H), 4.28 (m, 1H), 4.35 (m, 1H), 4 59 (m, 1H), 5 69 (AA , 2H), 5.52 (br, 1H), 6.02 (br, 1H), 6.58 (br, 1H), 6.86 (m, 3H), 7.13 (d, J=9Hz, 2H), 7.36 (m, 5H), 7.49 (br s, 1H), 8.20 (br, 1H).

EXAMPLE 197

6-(BenzYloxYcarbonyl)amino-6-carboxyhexanoyl-(4-OMe)Phe-His Amide 2(S)-Amino-1-cyclohexyl-3(R),4(S)-dihydroxy-6-methylheptane Using the procedure of Example 190 but replacing the resultant compound of Example 188 with the resultant compound of Example 196 gave the desired product, m.p. 144°-147° C. (dec). Mass spectrum: $(M+H)^+ = 849$. NMR $(d_6\text{-DMSO})$: 0.79 (d, J=7Hz, 3H), 0.87 (d, J=7Hz, 3H), 1.1-1.8 (br envelope), 2.03 (t, J=7Hz, 2H), 2.65 (m, 2H), 2.8-3.0 (m, 3H), 3.12 (m, 1H), 3.69 (s, 3H), 3 85 (m, 1H), 4.12 (m, 1H), 4.38 (m, 1H), 4.48 (m, 1H), 5.02 (s, 2H), 6.80 (m, 3H), 7.13 (d, J=9Hz, 2H), 7.35 (m, 5H), 7 43 (br d, 1H), 7.52 (br s, 1H), 8.10 (br, 1H), 8.30 (br, 1H).

EXAMPLE 198

6-(Benzyloxycarbonyl)amino-6-(methoxycarbonyl)hexanoyl-(4-OMe)Phe-His Amide of 2(S)-Amino-1-cyclohexyl-3(R),4(S)-dihydroxy-6-methylheptane Using the procedure of Example 192 but replacing the resultant compound of Example 55 with the resultant compound of Example 195 gave the desired compound, m.p. 155° C. Mass spectrum: $(M+H)^+ = 863$. NMR $(CDCl_3/CD_3OD)$: 1.40 (d, J=7Hz, 3H), 1.45 (d, J=7Hz, 1H), 1.1-1.9 (br envelope), 2.16 (t, J=7Hz, H), 2.85 (m, 1H), 2.97 (m, 1H), 3.14 (m, 2H), 3 29 (m, 1H), 3.37 (s, 3H), 3.79 (s, 3H), 4.21 (m, 2H), 4.38 (dd, J=10, 5Hz, 1H), 4.56 (m, 1H), 5.11 (s, 3H), 6.85 (m, 2H), 7.13 (m, 2H), 7.36 (s, 5H), 7.52 (m, 1H).

EXAMPLE 199

[5-(Benzyloxycarbonyl)amino-5-carboxypentyl]carbamoyl-(4-OMe)Phe Benzyl Ester

Using the procedure of Example 116 but replacing H-Phe-OMe HCl with L-tyrosine benzyl ester methyl ether HCl and replacing morpholine with N-alpha-benzyloxycarbonyllysine ave the desired compound.

EXAMPLE 200

[5-(Benzyloxycarbonyl)amino-5-(methoxycarbonyl)pentyl]carbamoyl-(4-OMe)Phe Benzyl Ester The resultant compound of Example 199 (I7 mmol) was allowed to react with excess diazomethane in ether. After removal of the solvent, purification by silica gel chromatography using 2:1 chloroform:ethyl acetate gave the desired compound. NMR $(CDCl_3)$ 1.33 (m, 2H), 1.45 (m, 2H), 1.65 (m, 1H), 1.78 (m, 1H), 2.96 (m, 2H), 3.11 (m, 2H), 3.73 (s, 6H), 4.32 (m, 1H), 4.68 (m, 1H), 4.78 (m, 1H), 4.90 (br d, J=9Hz, 1H), 5.0–5.2 (m, 4H), 5.64 (br d, J=9Hz), 6.71 (d, J=9Hz, 2H), 6.90 (d, J=9Hz, 2H), 7.3–7.4 (m, 10H).

EXAMPLE 201

[5-Amino-5-(methoxycarbonyl)pentyl]carbamoyl-(4-OMe)Phe-OH

Using the procedure of Example 193 with the resultant compound of Example 200 gave the desired compound.

EXAMPLE 202

[5-(t-Butyloxycarbonyl)amino-5-(methoxycarbonyl)-pentyl]carbamoyl-(4-OMe)Phe-OH

A suspension of 1.15 g (3.0 mmol) of the resultant compound of Example 201 in 100 ml of dichloromethane was treated with 0.46 ml (3.3 mmol) of triethylamine and 725 mg (3.3 mmol) of di-t-butylcarbonate. After stirring for 3 days, the solution was washed with aqueous HCl, dried and concentrated to give the desired compound.

EXAMPLE 203

[5-(t-Butyloxycarbonyl)amino-5-(methoxycarbonyl)-pentyl]-carbamoyl-(4-OMe)Phe-Leu Benzyl Ester The resultant compound of Example 202 was coupled to leucine benzyl ester hydrochloride using the procedure of Example 2 to the give the desired compound after purification by silica gel chromatography. Mass spectrum: $(M+H)^+=685$. NMR (CDCl$_3$): 0.87 (d, J=7Hz, 6H), 1.2–1.8 (br envelope), 1.44 (s, 9H), 2.98 (m, 2H), 3.12 (m, 2H), 3.73 (s, 3H), 3.77 (s, 3H), 4.25 (m, 1H), 4.52 (m, 2H), 4.68 (m, 1H), 4.94 (m, 1H), 5.13 (AA', 2H), 5.73 (br d, 1H), 6.48 (br d, 1H), 6.79 (d, J=9Hz, 2H), 7.11 (d, J=9Hz, 2H), 7.35 (m, 5H).

EXAMPLE 204

[5-(t-Butyloxycarbonyl)amino-5-(methoxycarbonyl)-pentyl]carbamoyl-(4-OMe)Phe-Leu-OH Using the procedure of Example 193 with the resultant compound of Example 203 gave the desired compound.

EXAMPLE 205

[5-(t-Butyloxycarbonyl)amino-5-(methoxycarbonyl)-pentyl]carbamoyl-(4-OMe)Phe-Leu Amide of 2(S)-Amino-1-cyclohexyl-3(R),4(S)-dihydroxy-6-methylheptane Using the procedure of Example 2 but replacing the resultant compound of Example 1 with the resultant 3(R),4(S) diastereomer of Example 14 and replacing Boc-Phe-Ala-OH with the resultant compound of Example 204 gave the desired compound, m.p 85°–87° C. Mass spectrum; $(M+H)^+=820$. NMR (CDCl$_3$): 0.9–1.0 (m, 12H), 1.1–2.0 (br envelope), 1.45 (s, 9H), 2.6 (m, 1H), 2.8–3.4 (m, 6H), 3.73 (s, 3H), 3.80 (s, 3H), 4.2 (m, 2H), 4.38 (m, 2H), 5.15 (br, 1H), 6.25 (br, 1H), 6.86 (d, J=9Hz, 2H), 7.12 (d, J=9Hz, 2H).

EXAMPLE 206

(5-Amino-5-carboxypentyl)carbamoyl-(4-OMe)Phe-Leu Amide of 2(S)-Amino-1-cyclohexyl-3(R),4(S)-dihydroxy-6-methylheptane The resultant compound of Example 205 (30 mg, 0.037 mmol) was dissoved in 2 ml of 4M HCl in dioxane and stirred at 0° C. for 2 h. After removing the solvent in vacuo, the residue was allowed to react according to the procedure of Example 190 to give a crude lithium salt which was neutralized to pH 7 and extracted with chloroform to give 9.2 mg of the desired compound, m.p. 177°–180° C. Mass spectrum; $(M+H)^+=706$. NMR (CD$_3$OD): 0.9 (m, 12H), 1.1–1.9 (br envelope), 2.90 (m, 1H), 3.0–3.2 (m, 2H), 3.5 (m, 1H), 3.77 (s, 3H), 4.3–4.4 (m, 2H), 6.83 (br d, 2H), 7.14 (br d, 2H).

EXAMPLE 207

2-N-methyl-benzyloxycarbonylaminoethanol

To N-methyl ethanolamine (149 mmol) in methylene chloride (100 ml) at 0° C. was added benzyl chloroformate (70 mmol). The mixture was stirred at 0° C. for 30 min, then at room temperature for 1 h, poured into ethyl acetate, washed with 2M HCl, saturated NaHCO$_3$ solution and then brine, then dried over Na$_2$SO$_4$ and evaporated to provide the desired compound. NMR (CDCl$_3$) 3.01 (s, 3H), 3.47 (m, 2H), 3.78 (m, 2H), 5.14 (s, 2H), 7.36 (m, 5H).

EXAMPLE 208

1-Methoxyethoxymethoxy-2-(N-methylbenzyloxycarbonylamino)ethane To the resultant compound from Example 207 (66.1 mmol) in methylene chloride (100 ml), was added diisopropylethylamine (138 mmol) and 2-methoxyethoxymethylchloride (132 mmol). After 4 h, the mixture was evaporated, dissolved in ethyl acetate, washed with 0.5M H saturated NaHCO$_3$ solution and then brine, then dried over Na$_2$SO$_4$ and evaporated to afford the desired product as an oil, b.p. 150°–170° C. (0.3 mm Hg).

EXAMPLE 209

1-Methylamino-2-methoxyethoxymethoxyethane

The resultant compound from Example 208 (31.2 mmol) and 10% palladium on carbon (3 g) in methanol (60 ml) were stirred under a hydrogen atmosphere for 24 h. The mixture was filtered, evaporated and distilled to afford the desired product as an oil, b.p. 130°–140° C., (45 mm Hg).

EXAMPLE 210

(2R)-2-Benzyl-3-(N-Methyl-N-2-methoxyethoxymethoxyethylamino-carbonyl) propionic Acid Using the procedure of Example 142 and replacing morpholine with the resultant compound from Example 209 gave the desired product. NMR (CDCl$_3$): 2.93, 2.97 (s, total 3H), 3.40, 3.41 (s, total 3H), 4.55,4.70 (m, total 2H), 7.27 (m, 5H).

EXAMPLE 211

(3,4-cis-Dihydroxypyrrolidinylcarbonyl)-(O-methyl)-tyrosine Methyl Ester

A suspension of L-(O-methyl)tyrosine methyl ester hydrochloride (10 g) in toluene (200 ml) was heated to 100° C. while phosgene gas was bubbled into the reaction mixture. After approximately 2 h, the mixture became homogeneous. The bubbling of phosgene was continued for 15 more minutes, keeping the temperature at about 100° C. The toluene was then evaporated and the residue was chased with benzene several times. The isocyanate from L-(Me)Tyr-OCH$_3$ was then dissolved in 100 ml of methylene chloride and 1.1 equivalent of 3-pyrroline (75% pure) was added dropwise at 0° C. After 15 min, the reaction mixture was washed with 0.5N HCl and methylene chloride. The organic layer was washed with aqueous NaHCO$_3$ and dried over MgSO$_4$ Evaporation of the solvent gave 3-pyrrolinylcarbonyl-(Me)Tyr-methyl ester, which was cis-hydroxylated under the following conditions: 2.5 g of the pyrrolinylcarbonyl(Me)Tyr-methyl ester was dissoved in 50 ml of THF and 1 ml of a 2.5% solution of OsO$_4$ in t-butanol was added, followed by 1.15 g of N-methylmorpholine-N-oxide. After 1 h, the solvent was evaporated and the residue dissolved in 150 ml of ethyl acetate and washed with dilute Na solution, saturated NaHCO$_3$ solution and then dried with MgSO$_4$ Evaporation of the solvent gave a gummy solid which was purified by SiO$_2$ column chromatography (5% MeOH/CH$_2$Cl$_2$) to give the desired compound. Mass spectrum: M$^+$ =338.

EXAMPLE 212

(3,4-cis-Dihydroxypyrrolidinylcarbonyl)-(O-methyl)-tyrosine

Using the procedure from Example 73 with the resultant compound from Example 211 and replacing ether extractions with chloroform extractions gave the desired product. Mass spectrum: M$^+$ =324.

EXAMPLE 213

N-[3,4-cis-di-(Methoxyethoxymethoxy)pyrrolidinylcarbonyl]-(O-methyl)Tyrosine

Using the procedure of Example 208 with the resultant compound from Example 211, followed by ester hydrolysis according to the procedure of Example 73, provided the desired product. NMR (CDCl$_3$): 3.08 (dd, 1H), 3.22 (dd, 1H), 3.38 (s, 3H), 3.39 (s, 3H), 3.80 (s, 3H), 4.24 (m, 2H), 4.45 (m, 1H), 4.63 (d., 1H), 4.82 (m, 4H), 6.85 (d, 2H), 7.13 (d, 2H).

EXAMPLE 214

(2R)-2-Benzyl-3-(N-methyl-N-2-methoxyethoxymethoxyethylamino-carbonyl)propionyl-His Amide of 2(S)-Amino-1-cyclohexyl-3(R),4(S)-dihydroxy-6-methylheptane Using the procedure of Example 21 but replacing TBA-CHA with the resultant compound of Example 210 gave the desired compound Anal. Calcd. for C$_{38}$H$_{61}$N$_5$O$_8$ 0.5 H$_2$O: C, 62.96; H, 8.62; N, 9.66. Found: C, 62.94; H, 8.57; N, 9.61.

EXAMPLE 215

N-[3,4-cis-di-(methoxyethoxymethoxy)pyrrolidinylcarbonyl]-(O-methyl) Tyrosine-His Amide of 2(S)-Amino-3(R),4(S)-dihydroxy-6-methylheptane Using the procedure of Example 21 but replacing TBA-CHA with the resultant compound from Example 213 gives the desired product.

EXAMPLE 216

(3,4-cis-dihydroxypyrrolidinylcarbonyl)-(O-methyl)-Tyr-His Amide of 2(S)-Amino-3(R),4(S)-dihydroxy-6-methylheptane Using the procedure of Example 2I but replacing TBA-CHA with the resultant compound of Example 2I1 gave the desired compound. Mass spectrum: (M+H)=687.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl., and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl-substituted compound of formula I which has been acylated with a blocked or unblocked amino acid residue, a phosphate function, or a hemisuccinate residue. The amino acid esters of particular interest are glycine and lysine; however, other amino acid residues can also be used. These esters serve as pro-drugs of the compounds of the present invention and serve to increase the solubility of these substances in the gastrointestinal tract. The preparation of the pro-drug esters is carried out by reacting a hydroxyl-substituted compound of formula I with an activated amino acyl, phosphoryl or hemisuccinyl derivative. The resulting product is then deprotected to provide the desired pro-drug ester.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with renin substrate (human angio- tensinogen) at 37° C. and pH 6.0. At the end of the incubation, the amount of angiotensin I formed is measured by radioimmunoassay and the molar concentration required to cause 50% inhibition, expressed as the $IC_{50}$, is calculated. When tested in accordance with the foregoing procedure, the compounds of the invention demonstrated $IC_{50}$'s in the range of $10^{-5}$ to $10^{-10}$ M as seen in Table I.

TABLE I

| Example Number | $IC_{50}$ (nM) | Example Number | $IC_{50}$ (nM) |
| --- | --- | --- | --- |
| 3 | 4000 | | |
| 6 | 50 | | |
| 15 | 1.5 | | |
| 16 | 70 | | |
| 17 | 35 | | |
| 18 | 95 | | |
| 21 | 2 | | |
| 22 | 1.5 | | |
| 23 | 10 | | |
| 24 | 2 | | |
| 25 | 20 | 81 | 0.6 |
| 26 | 1.5 | 82 | 0.6 |
| 27 | 7 | 83 | 0.6 |
| 28 | 80 | 84 | 10 |
| 29 | 0.6 | 85 | 0.4 |
| 30 | 0.75 | 87 | 0.55 |
| 31 | 1 | 88 | 0.6 |
| 32 | 2 | 89 | 1 |
| 33 | 5 | 90 | 0.4 |
| 34 | 1.5 | 91 | 0.3 |
| 35 | 1 | 92 | 0.5 |
| 36 | 0.4 | 93 | 0.55 |
| 37 | 0.5 | 97 | 0.3 |
| 39 | 2 | 101 | 5 |
| 43 | 5 | 102 | 0.6 |
| 46 | 1.5 | 103 | 1 |
| 47 | 1 | 108 | 0.55 |
| 49 | 2 | 111 | 0.5 |
| 54 | 0.95 | 114 | 1.3 |
| 55 | 2 | 115 | 1 |
| 56 | 5.5 | 118 | 0.5 |
| 57 | 7.5 | 124 | 0.65 |
| 58 | 7 | 127 | 0.75 |
| 61 | 0.55 | 141 | 5.5 |
| 62 | 2 | 143 | 0.3 |
| 63 | 0.45 | 169 | 6.0 |
| 64 | 3 | 173 | 0.9 |
| 67 | 0.8 | 174 | 12 |
| 68 | 1 | 178 | 2 |
| 69 | 0.81 | 179 | 1 |
| 70 | 2.5 | 180 | 0.8 |
| 74 | 0.7 | 183 | 12 |
| 75 | 0.4 | 184 | 0.59 |
| 76 | 0.5 | 185B | 0.51 |
| 77 | 0.98 | 186 | 2 |
| | | 189 | 1.1 |
| | | 190 | 0.34 |
| | | 192 | 0.61 |
| | | 193 | 0.74 |
| | | 194 | 2.3 |
| | | 196 | 0.57 |
| | | 198 | 0.59 |
| | | 205 | 2.6 |
| | | 206 | 3.9 |
| | | 214 | 0.24 |
| | | 216 | 0.9 |

The compounds of the invention may also be used with one or more antihypertensive agents selected from group consisting of diuretics, and/or β-adrenergic agents, central nervous system -acting agents, adrenergic neuron blocking agents, vasodilators, angiotensin I converting enzyme inhibitors, and other antihypertensive agents. Total daily dose administered to a host in le or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer s solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

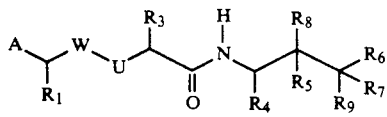

wherein A is $NR_{11}R_{12}$ wherein $R_{11}$ is hydrogen, loweralkyl, aminoalkyl, cyanoalkyl or hydroxyalkyl, and $R_{12}$ is carboxyalkyl, alkoxycarbonylalkyl, (amino)carboxylalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkyamino)alkoxycarbonylalkyl, ((N-protected)alkylamino)alkoxycarbonylalkyl or (dialkylamino)alkoxycarbonylalkyl;

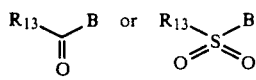

wherein B is NH, alkylamino, S, O, $CH_2$ or CHOH and $R_{13}$ is (dihydroxyalkyl)(alkyl)amino, carboxyalkoxyalkyl, (alkoxycarbonyl)alkoxyalkyl, carboxyalkyl, carboxyalkylamino, alkoxycarbonylalkyl, alkoxycarbonylalkylamino, (amino)carboxyalkyl, (amino)carboxyalkylamino, ((N-protected)amino)carboxyalkyl, ((N-protected)amino)carboxyalkylamino, (alkylamino)carboxyalkyl, (alkylamino)carboxyalkylamino, ((N-protected)alkylamino)carboxyalkyl, ((N-protected)alkylamino)carboxyalkylamino, (dialkylamino)carboxyalkyl, (dialkylamino)carboxyalkylamino, (amino)alkoxycarbonylalkyl, (amino)alkoxycarbonylalkylamino, ((N-protected)amino)alkoxycarbonylalkyl, ((N-protected)amino)alkoxycarbonylalkylamino, (alkyamino)alkoxycarbonylalkyl, (alkylamino)alkoxycarbonylalkylamino, ((N-protected)alkylamino)alkoxycarbonylalkyl, ((N-protected)alkylaminoalkoxycarbonylalkylamino, (dialkylamino)alkoxycarbonylalkyl or (dialkylamino)alkoxycarbonylalkylamino, aminocycloalkyl, aminoalkylamino, dialkylaminoalkyl(alkyl)amino, arylalkylamino, arylalkyl(alkyl)amino, alkoxyalkyl(alkyl)amino, (polyalkoxy)alkyl(alkyl)amino, di-(alkoxyalkyl)amino, di-(hydroxyalkyl)amino, di-((polyalkoxy)alkyl)amino, polyalkoxy, (polyalkoxy)alkyl, a saturated heterocyclic monosubstituted with alkoxy or polyalkoxy; a saturated heterocyclic disubstituted with substitutents selected from oxo, amino, alkylamino, dialkylamino, alkoxy, polyalkoxy and loweralkyl; or an unsaturated heterocyclic monosubstituted with alkoxy or polyalkoxy;

W is C=O or CHOH;

U is $CH_2$ or $NR_2$, provided that when W is CHOH, U is $CH_2$;

$R_1$ is loweralkyl, cycloalkymethyl, benzyl, 4-methoxybenzyl, halobenzyl, (1-naphthyl)methyl, (2-naphthyl)methyl, (4-imidazolyl)methyl, (alpha, alpha)-dimethylbenzyl, 1-benzyloxyethyl, phenethyl, phenoxy, thiophenoxy or anilino; provided if $R_1$ is phenoxy, thiophenoxy or anilino, B is $CH_2$ or CHOH; $R_2$ is hydrogen or loweralkyl; $R_3$ is loweralkyl, loweralkenyl, ((alkoxy)alkoxy)alkyl, (thioalkoxy)alkyl, benzyl or heterocyclic ring substituted methyl $R_4$ is loweralkyl. cycloalkylmethyl or benzyl; $R_5$ is vinyl, formyl, hydroxymethyl or hydrogen; $R_7$ is hydrogen or loweralkyl; $R_8$ and $R_9$ are independently selected from OH and $NH_2$; and $R_6$ is hydrogen, loweralkyl, vinyl or arlyalkyl; provided that when $R_5$ and $R_7$ are both hydrogen and $R_8$ and $R_9$ are OH, the carbon bearing $R_5$ is of the "R" configuration and the carbon bearing $R_6$ is of the "S" configuration; or a pharmaceutically acceptable salt or ester thereof.

2. The compound of claim 1 wherein $R_1$ is benzyl or 4-methoxybenzyl, $R_3$ is (4-imidazolyl)methyl and $R_4$ is cyclohexylmethyl.

3. The compound of claim 1 wherein $R_2$, $R_5$ and $R_7$ are hydrogen; and $R_6$ is isobutyl.

4. The compound of claim 1 wherein A is $NHR_{12}$ wherein $R_{12}$ is carboxyalkyl, (amino)carboxyalkyl, (alkylamino)carboxyalkyl, (dialkylamino)carboxyalkyl, alkoxycarbonylalkyl, (amino)alkoxycarbonylalkyl, (alkylamino)alkoxycarbonylalkyl or (dialkylamino)alkoxycarbonylalkyl, $R_1$ is benzyl or 4-methoxybenzyl and $R_2$ is hydrogen.

5. The compound of claim 1 wherein A is carboxyalkylcarbonylamino or (amino)carboxyalkylcarbonylamino, $R_1$ is benzyl or 4-methoxybenzyl and $R_2$ is hydrogen.

6. The compound of claim 1 wherein A is (alkylamino)carboxyalkylcarbonylamino or (dialkylamino)carboxyalkylcarbonylamino, $R_1$ is benzyl or 4-methoxybenzyl and $R_2$ is hydrogen.

7. The compound of claim 1 wherein A is (carboxyalkylamino)carbonylamino or carbonylamino, $R_1$ is benzyl or 4-methoxybenzyl and $R_2$ is hydrogen.

8. The compound of claim 1 wherein A is carbonylalkyl, $R_1$ is benzyl or 4-methoxybenzyl and $R_2$ is hydrogen.

9. A pharmaceutical composition for treating hypertension, comprising a pharmaceutical carrier and a therapeutically effective amount of a compound of claim 1.

10. A method for treating hypertension comprising administering to a host in need of such treatment a therapeutically effective amount of a compound of claim 1.

* * * * *

UNITED STATES PATENT AND TRADEMARK OFFICE
CERTIFICATE OF CORRECTION

PATENT NO. : 5,032,577

DATED : July 16, 1991

INVENTOR(S) : Anthony K. L. Fung; Dale J. Kempf; Jay R. Luly; Saul H. Rosenberg; Jacob J. Plattner It is certified that error appears in the above-identified patent and that said Letters Patent is hereby corrected as shown below:

Column 2, Line 40: Replace "hydroxyalkyl," with --hydroxyalkoxy,--

Column 3, Line 28: Replace "erters" with --esters--

Column 8, Line 33: Replace ""LYs"", with --"Lys"--

Column 8, Line 40: Replace "angiotensinogen Incor-" with --angiotensinogen. Incor- --

Column 7 & 8, Scheme I, last line: Replace "cycloadlkylmethyl" with --cycloalkylmethyl--

Column 9, Line 13: Replace "seguence" with --sequence--

Column 10, Line 25: Replace "hydrochleride" with --hydrochloride--

Column 10, Line 53: Replace "(55 g SiO2; 95:5, CH2C12:CH3OH)" with --SiO$_2$; 95:5, CH$_2$C$_{12}$:CH$_3$OH)--

Column 11, Line 37: Replace "Boc-Phe3His" with --Boc-Phe-His--

Column 11, Line 51: Replace "C$_{36}$H$_{59}$N$_5$O$_6$SI:" with --C$_{36}$H$_{59}$N$_5$O$_6$Si:--

Column 12, Line 15: Replace "(3 x 50" with --(3 x 150--

Column 12, Line 33: Replace "0.1 M H (pH=7)," with --0.1 M H$_3$PO$_4$ (pH=7),--

Column 13, Line 68: Replace "jM" with --M--

UNITED STATES PATENT AND TRADEMARK OFFICE
CERTIFICATE OF CORRECTION

PATENT NO. : 5,032,577

DATED : July 16, 1991

INVENTOR(S) : Anthony K. L. Fung; Dale J. Kempf; Jay R. Luly; Saul H. Rosenberg; Jacob J. Plattner.

It is certified that error appears in the above-identified patent and that said Letters Patent is hereby corrected as shown below:

Column 15, Line 22: Replace "C, 6.8;" with --C,66.8;--

Column 16, Line 58: After the word "but" insert --replacing--

Column 16, Line 67: After the word "but" insert --replacing--

Column 17, Line 31 and 32: Replace "6-methylhectane" with --6-methylheptane--

Column 17, Line 33: After the word "but" insert --replacing--

Column 17, Line 43: After the word "but" insert --replacing--

Column 17, Line 64: After the word "but" insert --replacing--

Column 18, Line 18: After the word "but" insert --replacing--

Column 18, Line 38 & 39: Replace "dihYdroxy-6-methYlheptane" with --dihydroxy-6-methylheptane--

Column 18, Line 64: After the word "but" insert --replacing--

Column 19, Line 7: After the word "but" insert --replacing--

Column 19, Line 14: Replace (N,Me, NTMBn) should read (N Me, $N_{IM}Bn$).

Column 19, Line 17: After the word "but" insert --replacing--

Column 19, Line 26: Replace "-1-clohexyl-3" with -- -1-cyclohexyl-3 --

Column 19, Line 60: Replace "-dihYdroxY-7-" with --dihydroxy-7---

Column 19, Line 61: Replace "methYloctane" with --methyloctane--

UNITED STATES PATENT AND TRADEMARK OFFICE
CERTIFICATE OF CORRECTION

PATENT NO. : 5,032,577

DATED : July 16, 1991

INVENTOR(S) : Anthony K. L. Fung; Dale J. Kempf; Jay R. Luly; Saul H. Rosenberg; Jacob J. Plattner It is certified that error appears in the above-identified patent and that said Letters Patent is hereby corrected as shown below:

Column 21, Line 36: Replace "EthoxycarbonYl-" with --Ethoxycarbonyl- --

Column 21, Line 47: Replace "(N-ButYl,4-$OCH_3$)" with (N-Butyl,4-$OCH_3$) --

Column 21, Line 48: Replace "(4-OCH3)" with --(4-$OCH_3$)--

Column 22, Line 8: Replace "(3-I,4- $QCH_3$)" with (3-I,4- $OCH_3$)--

Column 22, Line 11: Replace "NaOAc $3H_2O$" with --NaOAc.$3H_2O$--

Column 22, Line 27: Replace "(1 atmosphere H)" with --(1 atmosphere $H_2$)--

Column 22, Line 37: Replace "-dihydroxY-" with --dihydroxy- --

Column 22, Line 40: Replace "(3-I,4-OCH3)" with --(3-I,4-$OCH_3$)--

Column 22, Line 41: Replace "NaOAc.$3H_3O$" with --NaOAc.$3H_2O$--

Column 23, Line 42: Replace "Cbz-Sar-phe-His" with --Cbz-Sar-Phe-His--

Column 30, Line 28: Replace "=16" with ---=616--

Column 30, Line 31: Replace "EXAMPLE 1-2" with --EXAMPLE 102--

Column 30, Line 63: Replace "Acetyl-8-Ala-Phe-His" should read --Acetyl- -Ala-Phe-His--

Column 30, Line 68: Replace "Acetyl-8-Ala-Phe" should read "Acetyl- -Ala Phe

Column 32, Line 56: Replace "90°14 100°C." with --90°-100°C.--

UNITED STATES PATENT AND TRADEMARK OFFICE
CERTIFICATE OF CORRECTION

PATENT NO. : 5,032,577                                       Page 4 of 6
DATED      : July 16, 1991
INVENTOR(S) : Anthony K. L. Fung; Dale J. Kempf; Jay R. Luly;
              Saul H. Rosenberg; Jacob J. Plattner It is certified that error appears in the above-identified patent and that said Letters Patent is hereby corrected as shown below:

Column 32, Line 64: Replace "0 5N HC1" with --0.5N HC1--

Column 34, Line 2: Before the word "the" insert the word --Using--

Column 34, Line 37: Replace the word "Having" with the word --Using--.

Column 35, Line 17: Replace "(3-HydroxYpiperidinyl)"with
                    --(3-Hydroxypiperidinyl)--

Column 35, Line 26: Replace "4 96 g," with --4.96 g--

Column 36, Line 31: Replace "95/5-90/1)" with --95/5 - 90/10)--

Column 38, Line 6: Replace "495)" with --3495)--

Column 38, Line 17: Replace "-dihYdroxY-6-" with -- -dihydroxy-6- --

Column 39, Line 4: Replace "23° C.," with -- -23° C.,--

Column 39, Line 30: After "lated" and before "acetic" insert --using--

Column 39, Line 58: Replace "cYclohexYl" with --cyclohexyl--

Column 40, Line 33: Replace "(0 075 mmol)" with --(0.075 mmol)--

Column 41, Line 2: After "EXAMPLE 168" insert --(2S,3R,5R,8S,9R,10S)-7-Aza-

UNITED STATES PATENT AND TRADEMARK OFFICE
CERTIFICATE OF CORRECTION

PATENT NO. : 5,032,577

DATED : July 16, 1991

INVENTOR(S) : Anthony K. L. Fung; Dale J. Kempf; Jay R. Luly; Saul H. Rosenberg; Jacob J. Plattner It is certified that error appears in the above-identified patent and that said Letters Patent is hereby corrected as shown below:

Column 43, Line 65: Replace "NaHCO3," with --$NaHCO_3$,--

Column 45, Lines 20 and 21: Replace " 7 3" with --7.3--

Column 46, Line 10: Replace "Example 57." with --Example 157.--

Column 46, Line 23: Replace "1-cYclohexYl-3" with --1-cyclohexyl-3--

Column 47, Line 8: Replace "(BenzYloxYcarbonyl)" with --(Benzyloxycarbonyl)--

Column 48, Line 21: Replace "(BenzYloxYcarbonyl)" with _-(Benzyloxycarbonyl)--

Column 48, Line 59: Replace "ave" with --gave--

Column 50, Line 39: Replace "0.5M H" with --0.5M $H_3PO_4$,--

UNITED STATES PATENT AND TRADEMARK OFFICE
CERTIFICATE OF CORRECTION

PATENT NO. : 5,032,577
DATED : July 16, 1991
INVENTOR(S) : Anthony K.L. Fung, Dale J. Kempf; Jay R. Luly; Saul H. Rosenberg; Jacob J. Plattner It is certified that error appears in the above-indentified patent and that said Letters Patent is hereby corrected as shown below:

Column 51, Line 12: After "$MgSO_4$" add --.--

Column 51, Line 21: Replace "Na solution" with --$Na_2SO_3$ solution,--

Column 51, Line 22: After "$MgSO_4$" insert --.--

Signed and Sealed this

Twenty-eighth Day of December, 1993

Attest:

BRUCE LEHMAN

*Attesting Officer*   *Commissioner of Patents and Trademarks*